(12) United States Patent
Mao et al.

(10) Patent No.: US 12,048,532 B2
(45) Date of Patent: Jul. 30, 2024

(54) SURGICAL ELEVATOR OXIMETER

(71) Applicant: ViOptix, Inc., Newark, CA (US)

(72) Inventors: Jimmy Jian-Min Mao, Fremont, CA (US); Robert E. Lash, Redwood City, CA (US)

(73) Assignee: ViOptix, Inc., Newark, CA (US)

( * ) Notice: Subject to any disclaimer, the term of this patent is extended or adjusted under 35 U.S.C. 154(b) by 819 days.

(21) Appl. No.: 17/109,064

(22) Filed: Dec. 1, 2020

(65) Prior Publication Data

US 2021/0076997 A1 Mar. 18, 2021

Related U.S. Application Data

(60) Division of application No. 12/194,508, filed on Aug. 19, 2008, now Pat. No. 10,849,535, which is a continuation-in-part of application No. 29/321,861, filed on Jul. 24, 2008, now Pat. No. Des. 593,201, and a continuation-in-part of application No. 29/298,459, filed on Dec. 5, 2007, now Pat. No. Des. 575,398.

(51) Int. Cl.
A61B 5/145 (2006.01)
A61B 1/32 (2006.01)
A61B 5/00 (2006.01)
A61B 5/1459 (2006.01)

(52) U.S. Cl.
CPC ............ *A61B 5/14542* (2013.01); *A61B 1/32* (2013.01); *A61B 5/1459* (2013.01); *A61B 5/411* (2013.01); *A61B 5/4893* (2013.01)

(58) Field of Classification Search
CPC ..... A61B 5/14542; A61B 1/32; A61B 5/1459; A61B 5/411; A61B 5/4893

USPC ....... 600/201, 202, 219, 223, 213, 218, 245, 600/210, 227, 212, 215, 206, 235; 606/207, 160, 84
See application file for complete search history.

(56) References Cited

U.S. PATENT DOCUMENTS

| | | |
|---|---|---|
| 3,394,700 A | 7/1968 | Yamamoto |
| 3,729,006 A | 4/1973 | Wilder et al. |
| 3,769,974 A | 11/1973 | Smart et al. |
| 3,776,240 A | 12/1973 | Woodson |
| D235,549 S | 6/1975 | Funderburk |
| 4,049,000 A | 9/1977 | Williams |
| 4,190,042 A | 2/1980 | Sinnreich |
| 4,226,228 A | 10/1980 | Shin et al. |
| 4,945,896 A * | 8/1990 | Gade .......... A61B 5/14553 600/206 |
| 4,959,067 A | 9/1990 | Muller |
| D312,306 S | 11/1990 | Michelson |
| D318,116 S | 7/1991 | Michelson |
| 5,230,621 A | 7/1993 | Jacoby |
| 5,769,781 A | 6/1998 | Chappuis |
| 5,891,018 A | 4/1999 | Wells |
| D442,687 S | 5/2001 | Schulz |

(Continued)

OTHER PUBLICATIONS

Delta Surgical Instruments Product Catalog, Jun. 2006, pp. 35-39.

(Continued)

*Primary Examiner* — Eduardo C Robert
*Assistant Examiner* — Tara Rose E Carter
(74) *Attorney, Agent, or Firm* — Aka Chan LLP

(57) ABSTRACT

A surgical elevator has an oximeter sensor at its tip, which allows measuring of oxygen saturation of a tissue.

37 Claims, 18 Drawing Sheets

(56) References Cited

U.S. PATENT DOCUMENTS

| | | | |
|---|---|---|---|
| 6,309,219 B1 | 10/2001 | Robert | |
| 6,322,499 B1 * | 11/2001 | Evans | A61B 17/00008 600/245 |
| 6,416,465 B2 | 7/2002 | Brau | |
| 6,602,188 B2 | 8/2003 | Bolser | |
| D522,140 S | 5/2006 | Stalcup et al. | |
| 7,153,279 B2 | 12/2006 | Ayad | |
| D535,744 S | 1/2007 | Wright | |
| 7,226,413 B2 | 6/2007 | McKinley | |
| 7,261,689 B2 | 8/2007 | Holland et al. | |
| 10,849,535 B2 * | 12/2020 | Mao | A61B 5/1459 |
| 2002/0062070 A1 | 5/2002 | Tschupp et al. | |
| 2004/0260161 A1 | 12/2004 | Melker et al. | |
| 2007/0129608 A1 | 6/2007 | Sandhu | |

OTHER PUBLICATIONS

Elevators, Codman Surgical Product Catalog, S-53-S-60, N-162, (2004).

* cited by examiner

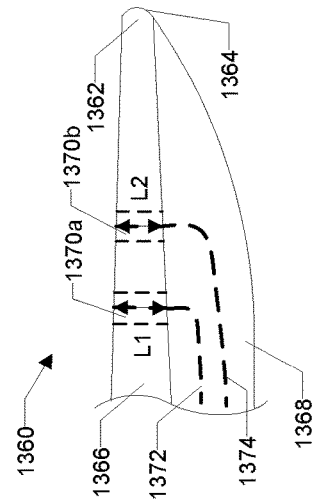
Figure 13
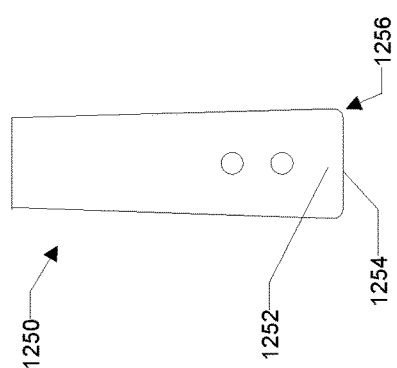
Figure 12
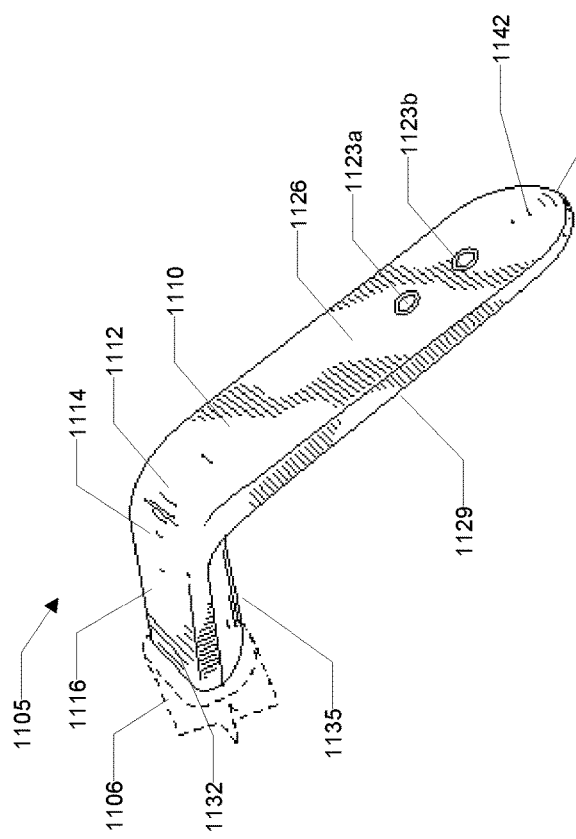
Figure 11
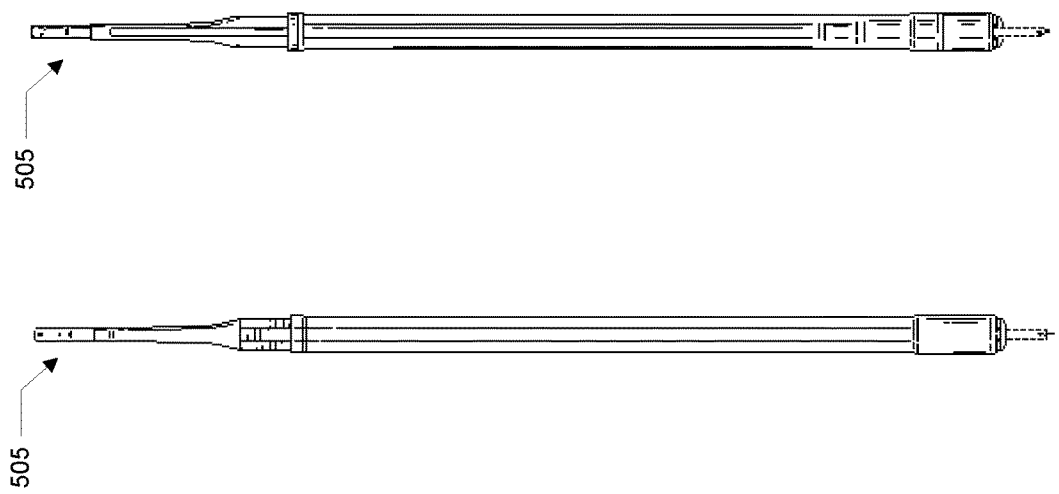
Figure 10
Figure 9

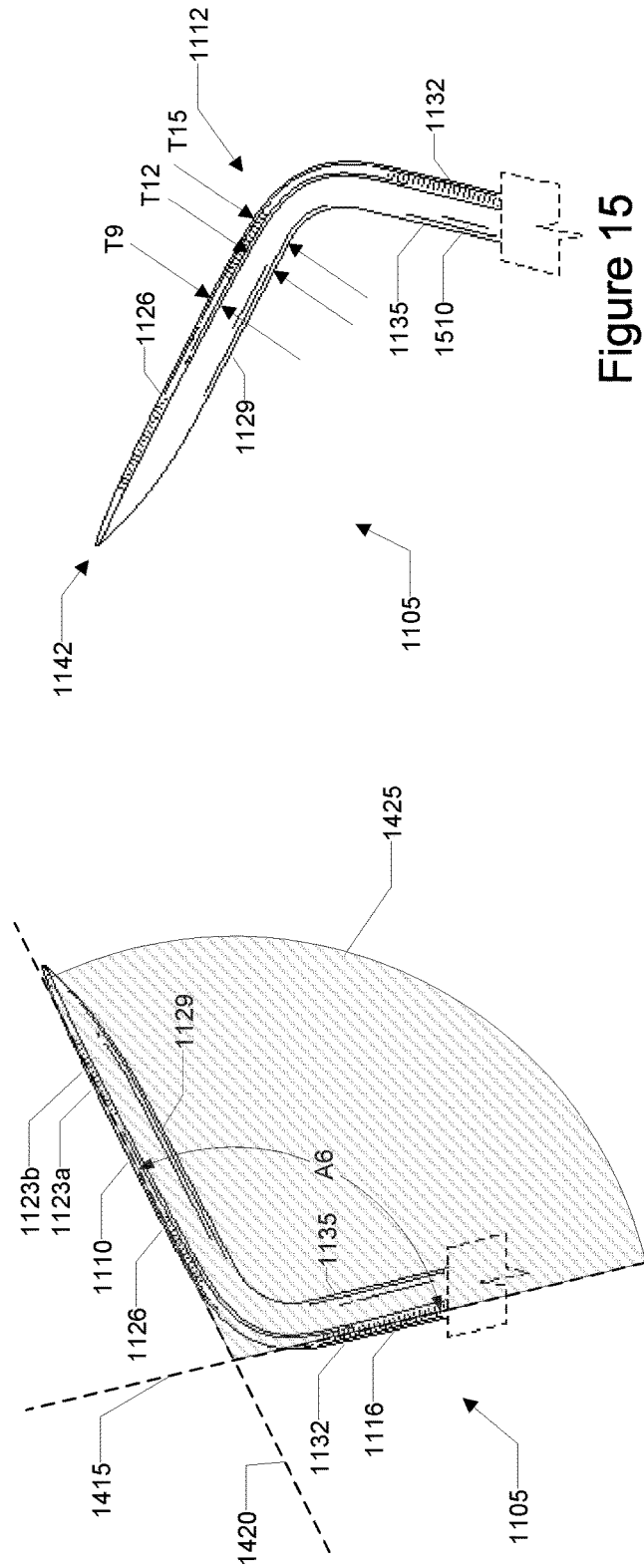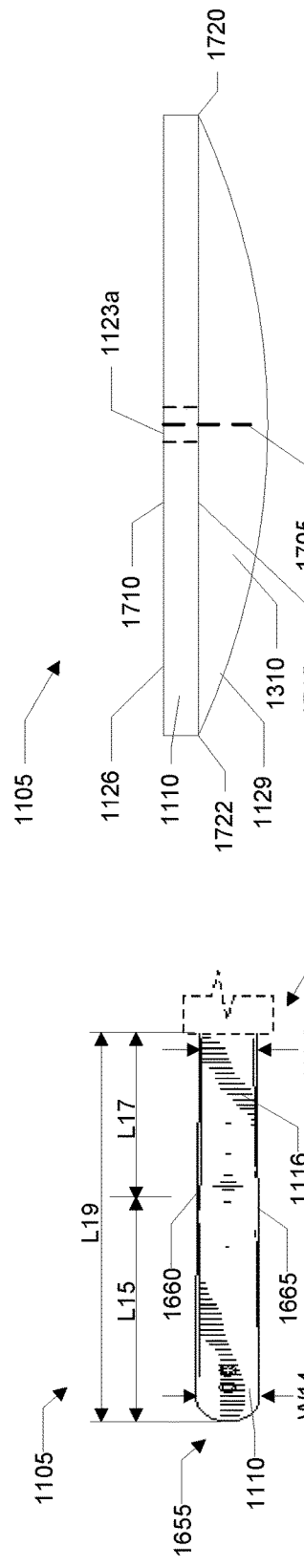

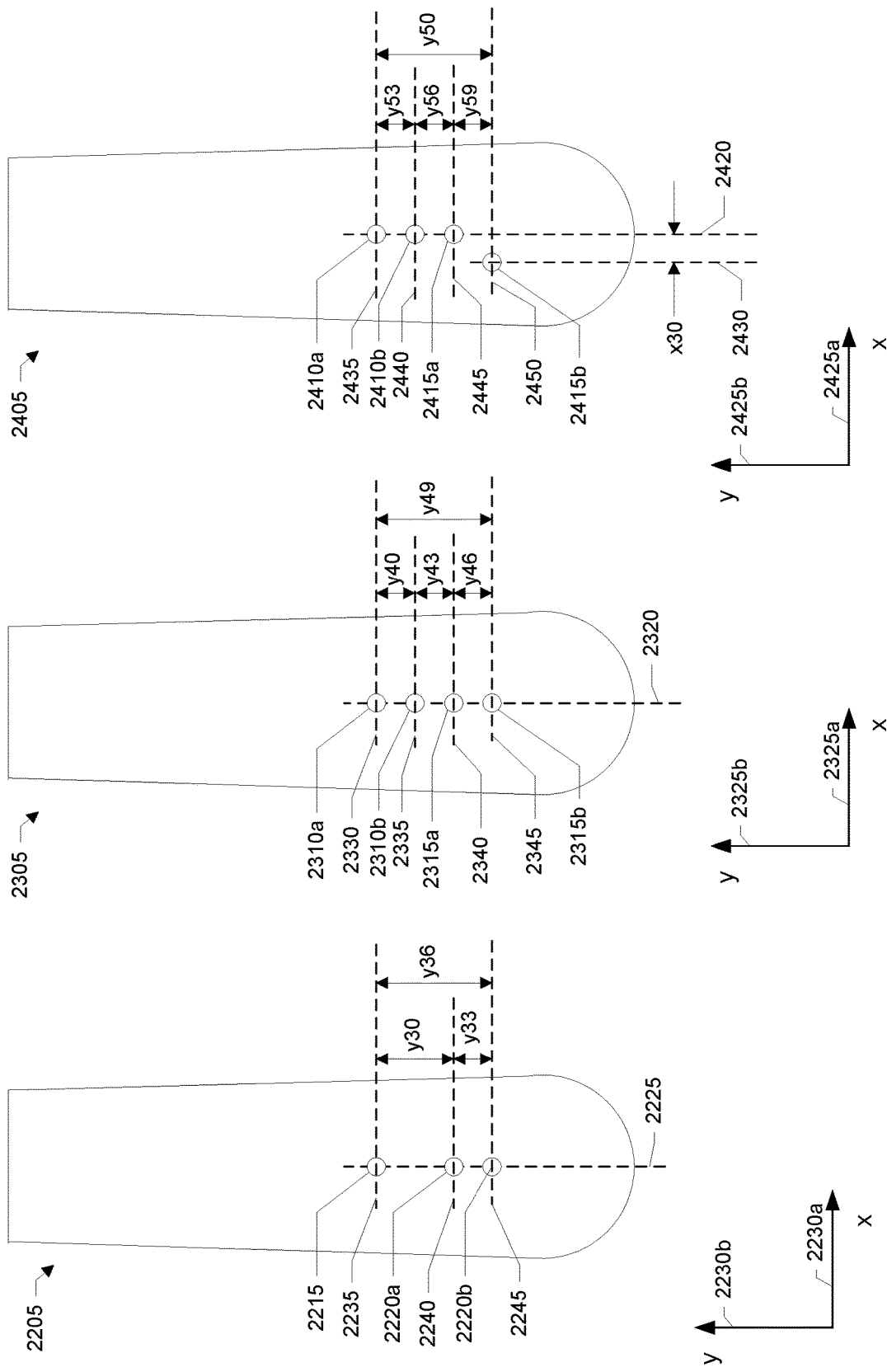

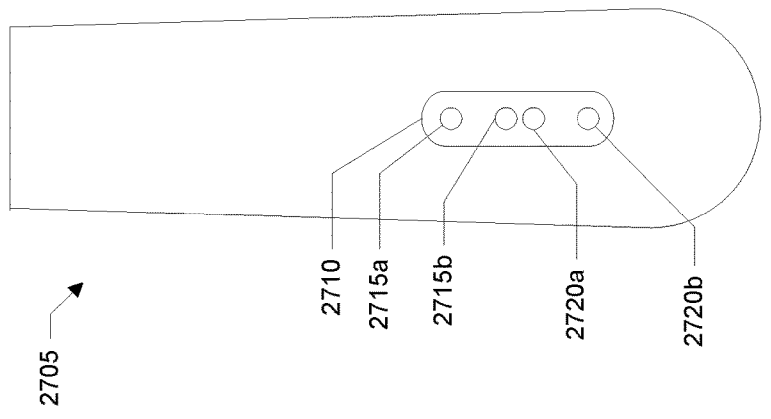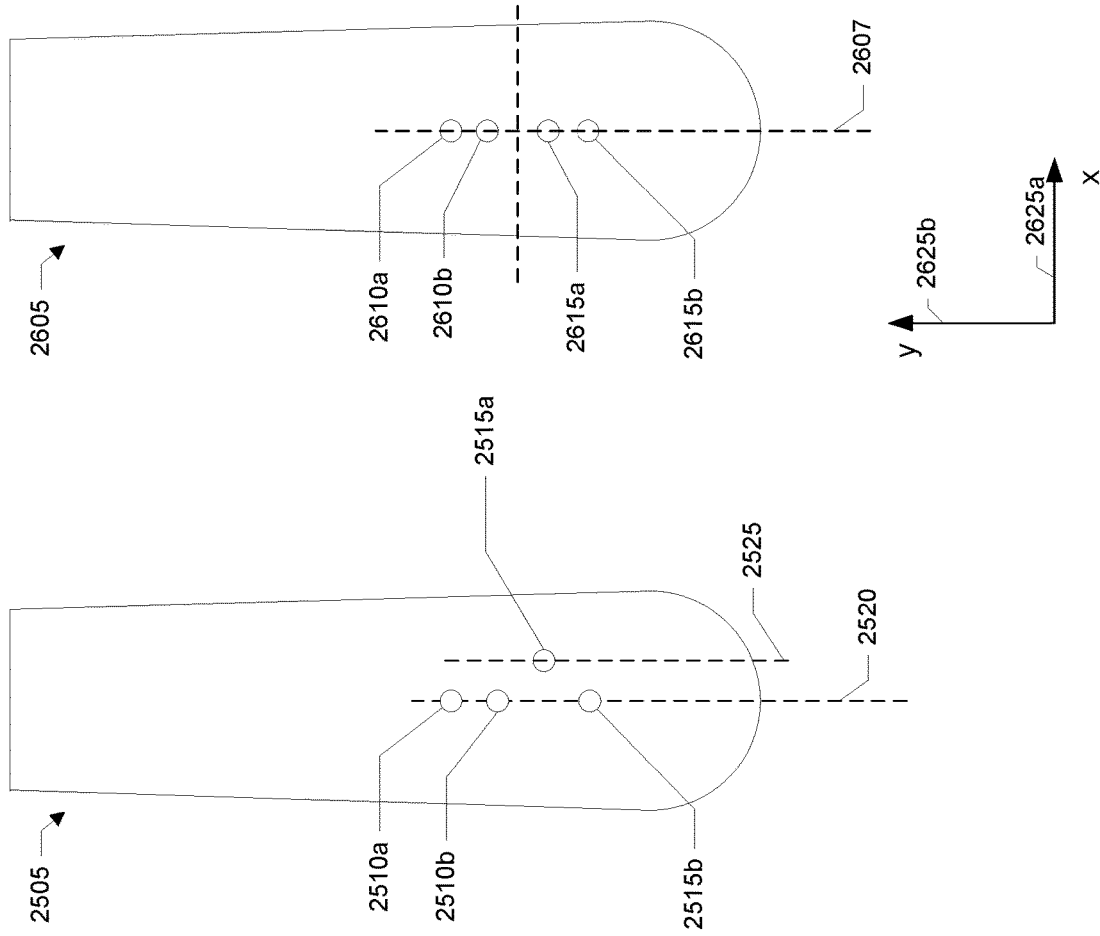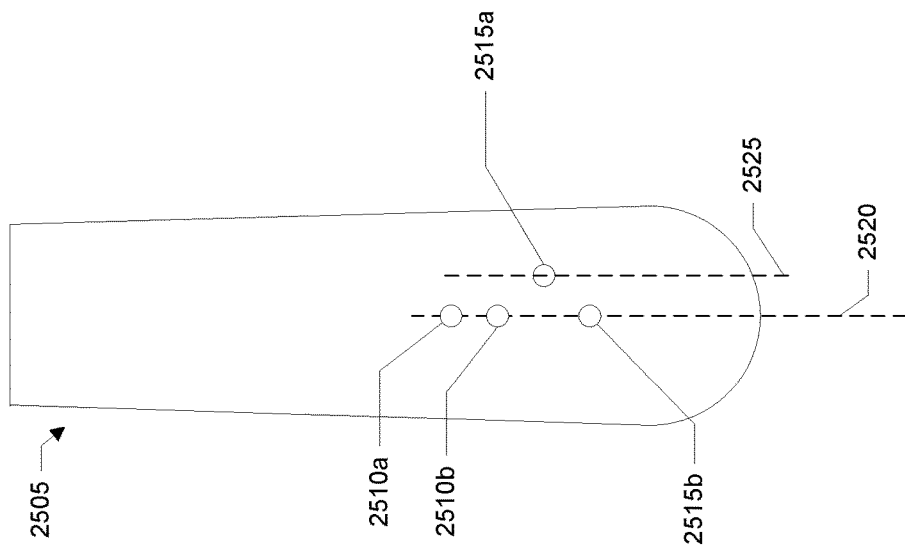
Figure 27
Figure 26
Figure 25

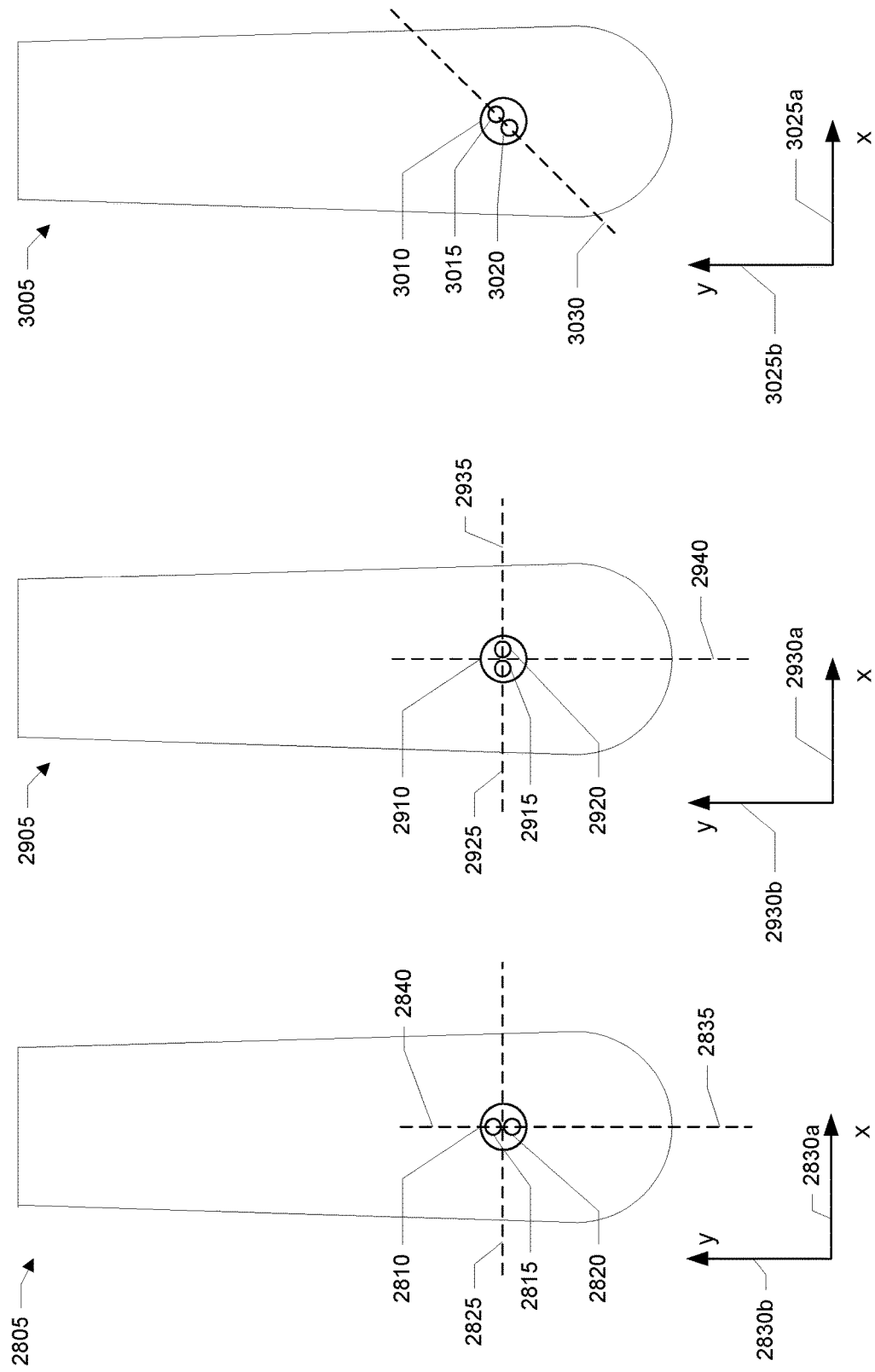

SURGICAL ELEVATOR OXIMETER

CROSS-REFERENCE TO RELATED APPLICATIONS

This patent application is a divisional of U.S. patent application Ser. No. 12/194,508, filed Aug. 19, 2008, issued as U.S. Pat. No. 10,849,535 on Dec. 1, 2020, which is a continuation-in-part of U.S. design patent application Ser. No. 29/321,861, filed Jul. 24, 2008, and Ser. No. 29/298,459, filed Dec. 5, 2007, issued as U.S. Pat. D575,398 on Aug. 19, 2008. These applications are incorporated by reference along with all other references cited in this application.

BACKGROUND OF THE INVENTION

This invention relates to the field of medical devices and more specifically to a surgical elevator with an oximeter sensor.

Surgical elevators play an important role in medicine. Depending on the surgical procedure, elevators may be used to measure, elevate, manipulate, or cut. One area of medicine in which surgical elevators are typically used is during spinal surgery.

Tens of thousands of spinal surgeries are performed each year. The number of spinal surgeries is continuing to increase due, in part, to an aging population, active lifestyles, and a better understanding of what causes back pain. Back pain may be due to disc herniation, degenerative disc disease, spinal trauma, and osteoarthritis just to name a few examples.

The spinal column includes a number of bony vertebrae. The vertebrae are separated by intervertebral discs which sit between adjacent vertebrae. The intervertebral discs help to distribute force between vertebrae. However, aging, trauma, and disease can cause the intervertebral discs to deteriorate. The deterioration may lead to a rupture or herniation of the disc. In some cases, this rupture or herniation of the intervertebral disc causes the disc to press on or compress a spinal nerve.

The effect of nerve compression is often severe back or neck pain, numbness, weakness, and in some cases paralysis.

A discectomy is one procedure that may be used to address a ruptured or herniated disc. A discectomy is the surgical removal of herniated disc material that presses on a nerve root or spinal cord. Surgical elevators are sometimes used to help gauge the gap between the nerve and other tissue. There is, however, a need for improved surgical elevators that help users (e.g., doctors and surgeons) know whether the gap will be sufficient.

If the gap is insufficient, then the nerve will continue to be compressed which may result in permanent damage to the nerve. This can be catastrophic because the nerves help to control the body's function including vital organs, sensation, and movement.

Therefore, there is a need to provide improved systems and techniques for surgical elevators.

BRIEF SUMMARY OF THE INVENTION

A surgical elevator has an oximeter sensor at its tip, which allows measuring of oxygen saturation of a tissue. In one embodiment, the tip includes one or more openings for at least one source and detector. In another embodiment, the tip includes an electronic component mounted at the tip. A specific implementation is a Woodson elevator with an oximeter sensor.

In an embodiment, a device includes a blade including a first side and a second side, where a first opening passes from the first side to the second side of the blade, and a second opening passes from the first side to the second side of the blade, a first optical fiber coupled to the first opening, a second optical fiber coupled to the second opening, and an epoxy, covering the first and second optical fibers and the first and second openings on the first side, where the first and second openings are unconcealed on the second side and a distal end of the blade is rounded. In a specific embodiment, the device is included with an endoscopic instrument.

The distal end may have a thickness of about 2 millimeters or less. A thickness between the first side and second side of the blade may be tapered, decreasing in thickness from a proximal end of the blade to the distal end of the blade.

The surface of the epoxy may be rounded from a first side edge to a second side edge of the blade. A thickness of the epoxy may be greater over the first and second openings than at the first and second side edges.

In an embodiment, a line passing through the first and second openings on the second side is parallel with a first side edge along the second side of the blade. A first distance from the first opening to the first side edge may be the same as a second distance from the first opening to a second side edge, opposite of the first side edge. The first side edge may be parallel to the second side edge.

A first distance from the first opening to the distal end may be shorter than a second distance from the first opening to a proximal end. A third distance from the second opening to the distal end may be longer than the first distance.

A first thickness from the first opening at the second side to an epoxy surface covering the first opening may be thinner than a second thickness from the second opening at the second side to an epoxy surface covering the second opening.

The blade may be metal. In an embodiment, the blade may further include a first portion and a second portion, the first portion being angled with respect to the second portion, and the first and second openings are in the first portion. The angle between the first and second portion may be in a range between about 90 degrees and 170 degrees.

In an embodiment, the blade comprises at most two openings.

In a further embodiment, the first optical fiber is a split optical fiber capable of carrying at least two optical channels.

In another embodiment, the first optical fiber is a concentric optical fiber capable of carrying at least two optical channels.

In a specific embodiment, a device includes a blade including a first side and a second side, where a first opening passes from the first side to the second side of the blade, a second opening passes from the first side to the second side of the blade, and a first length of the first opening is less than a second length of the second opening, a first optical fiber coupled to the first opening, a second optical fiber coupled to the second opening, and a resin, covering the first and second optical fibers and the first and second openings on the first side. A distal end of the blade may be rounded. In a specific embodiment, the device is included with an endoscopic instrument.

In embodiment, a method includes providing a metal blade having a tapered thickness, creating a first opening through the blade at a first position, creating a second opening though the blade at a second position, where the second opening has a length different from the first opening, attaching a first optical fiber to the blade at the first opening, attaching a second optical fiber to the blade the second opening, and covering the first and second optical fibers with an adhesive material.

The blade may include a first portion and a second portion, the first portion being angled with respect to the second portion, and the first and second openings are in the first portion. The blade may be coupled to an elongated handle and the first and second optical fibers may be run along the elongated handle.

The adhesive material may cover an entirety of one side of the metal blade. The adhesive material may include an epoxy.

In an embodiment, a method of operating a device includes a blade including a first side and a second side, where a first opening passes from the first side to the second side of the blade, a second opening passes from the first side to the second side of the blade, and a first length of the first opening is less than a second length of the second opening, a first optical fiber coupled to the first opening, and a second optical fiber coupled to the second opening.

The method includes emitting a first radiation emission through the first optical fiber to the first opening, receiving a second radiation emission at the second opening and transmitting the second radiation emission through the second optical fiber, and calculating a value based on quantities for the first radiation emission and second radiation emission and a distance between the first and second openings. The second radiation emission may be an attenuated reflection of the first radiation emission.

In an embodiment, a device includes a blade including a first side and a second side, where a first opening passes from the first side to the second side of the blade, a first optical fiber connected to the first opening, and an epoxy, covering the first optical fiber and the first opening on the first side, where the first opening is unconcealed on the second side and a distal end of the blade is rounded.

The device may further include an electronic component, mounted on the second side of the blade or mounted on the first side of the blade. The electronic component is at least one of a printed circuit board comprising power and ground wires, thin-film circuit board, a photodetector, a light emitting diode, or a laser diode. There may be a second opening, below the electronic component and extending through to the second side of the blade.

In an embodiment, a device includes a blade including a first side and a second side where a thickness of the blade between the first side and the second side decreases from a proximal end of the blade to a distal end of the blade, and a first electronic component, mounted on the second side of the blade.

In one embodiment, the first electronic component includes at least one of a printed circuit board including power and ground wires, thin-film circuit board, a photodetector, flexible circuit board, a light emitting diode, or a laser diode.

In another embodiment, the first electronic component includes a thin-film circuit board including at least one of a first radiation source, second radiation source, or a photodetector.

A first opening may pass from the first side to the second side of the blade, where the first opening is coupled to a first optical fiber.

In a specific embodiment, the first electronic component, mounted on the second side of the blade is replaced by a second electronic component, mounted on the first side of the blade, and the device further includes a first opening, below the second component and extending through to the second side of the blade.

The blade may include a cavity within which the first electronic component is mounted.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 9 shows a top view of the elevator.

FIG. 10 shows a bottom view of the elevator.

FIG. 11 shows a perspective of the tip of the elevator.

FIG. 12 shows a front view of a tip with rounded corners.

FIG. 13 shows a longitudinal cross section view of a tapered tip.

FIG. 14 shows a right-hand side view of the tip.

FIG. 15 shows a left-hand side view of the tip.

FIG. 16 shows a top view of the tip.

FIG. 17 shows a cross section of the tip.

FIG. 22 shows a front view of another embodiment of a first blade portion with a single light source and two detector asymmetrical array.

FIG. 23 shows a front view of a first blade portion with a two light source and two detector symmetrical array.

FIG. 24 shows a front view of a first blade portion with a two light source and two detector asymmetrical array.

FIG. 25 shows a front view of another embodiment of a first blade portion with a two light source and two detector asymmetrical array.

FIG. 26 shows a front view of a further embodiment of a first blade portion with a two light source and two detector symmetrical array.

FIG. 27 shows a front view of a first blade portion with multiple optical fiber bundles in a single opening.

FIG. 28 shows a front view of another embodiment of a first blade portion with multiple optical fiber bundles in a single opening.

FIG. 29 shows a front view of further embodiment of a first blade portion with multiple optical fiber bundles in a single opening.

FIG. 30 shows a front view of further embodiment of a first blade portion with multiple optical fiber bundles in a single opening.

DETAILED DESCRIPTION OF THE INVENTION

Figure 1:
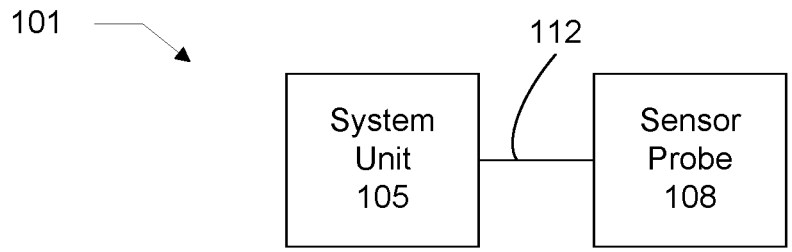
FIG. 1 shows an oximeter system for measuring oxygen saturation of tissue in a patient.

FIG. 1 shows an oximeter system 101 for measuring oxygen saturation of tissue in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers). In other implementations of the invention, however, connection 112 may be wireless such as via a radio frequency (RF) or infrared communication.

Typically, the system is used by placing the sensor probe in contact or close proximity to tissue (e.g., skin or nerve) at a site where an oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery. The tissue oximeter can make oxygen saturation measurements of tissue where there is no blood flow or pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbencies of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

Figure 2:
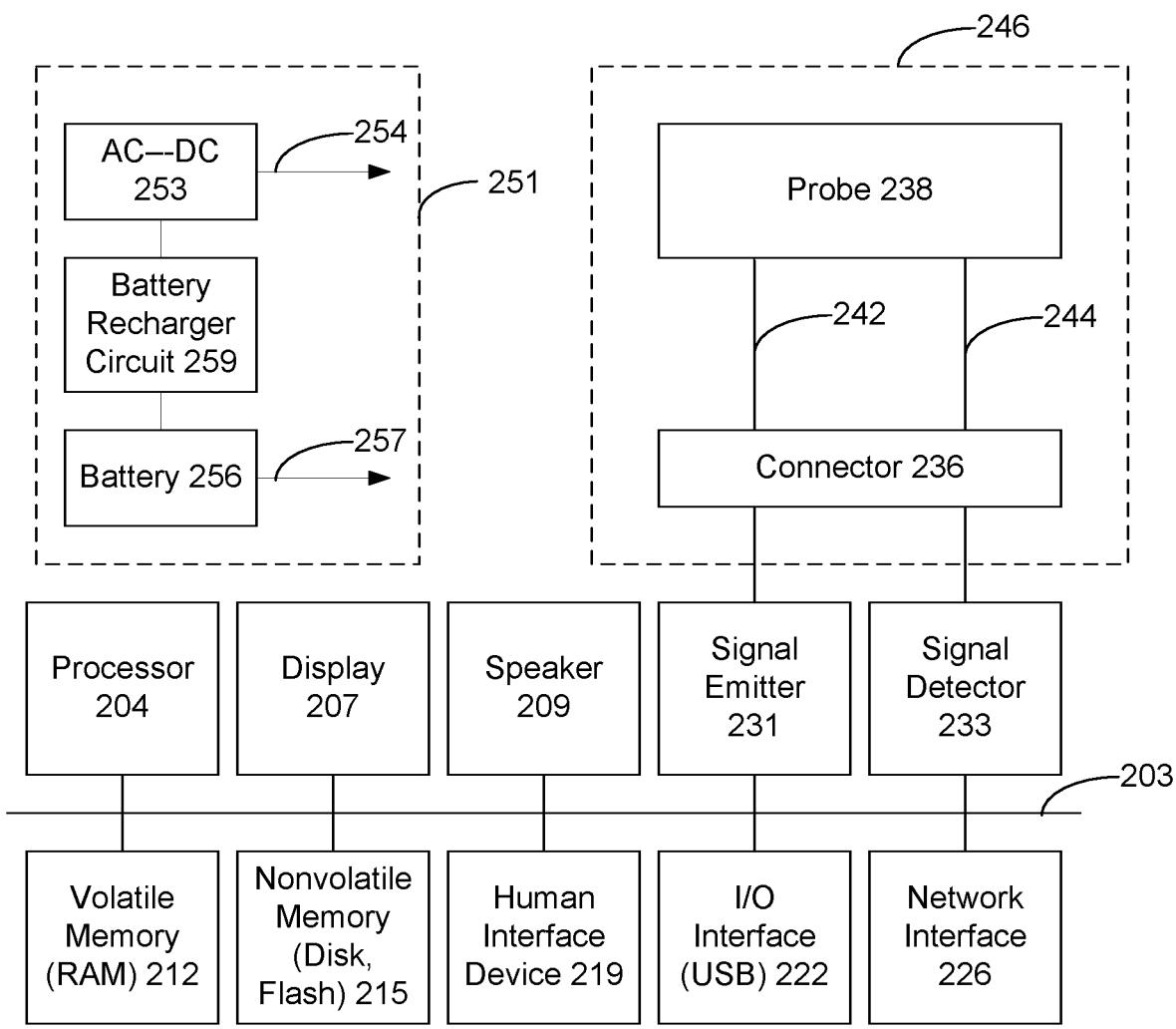
FIG. 2 shows detail of a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

The connector may have a locking feature; e.g., insert connecter, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. The second keying feature will let the system unit know which type of probe is connected, so that it can perform the right functionality, use the proper algorithms, or otherwise make adjustments in its the operation for a specific probe type.

In various implementations, the system is powered using a wall outlet or battery powered, or both. Block 251 shows power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from The MathWorks, Inc.), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
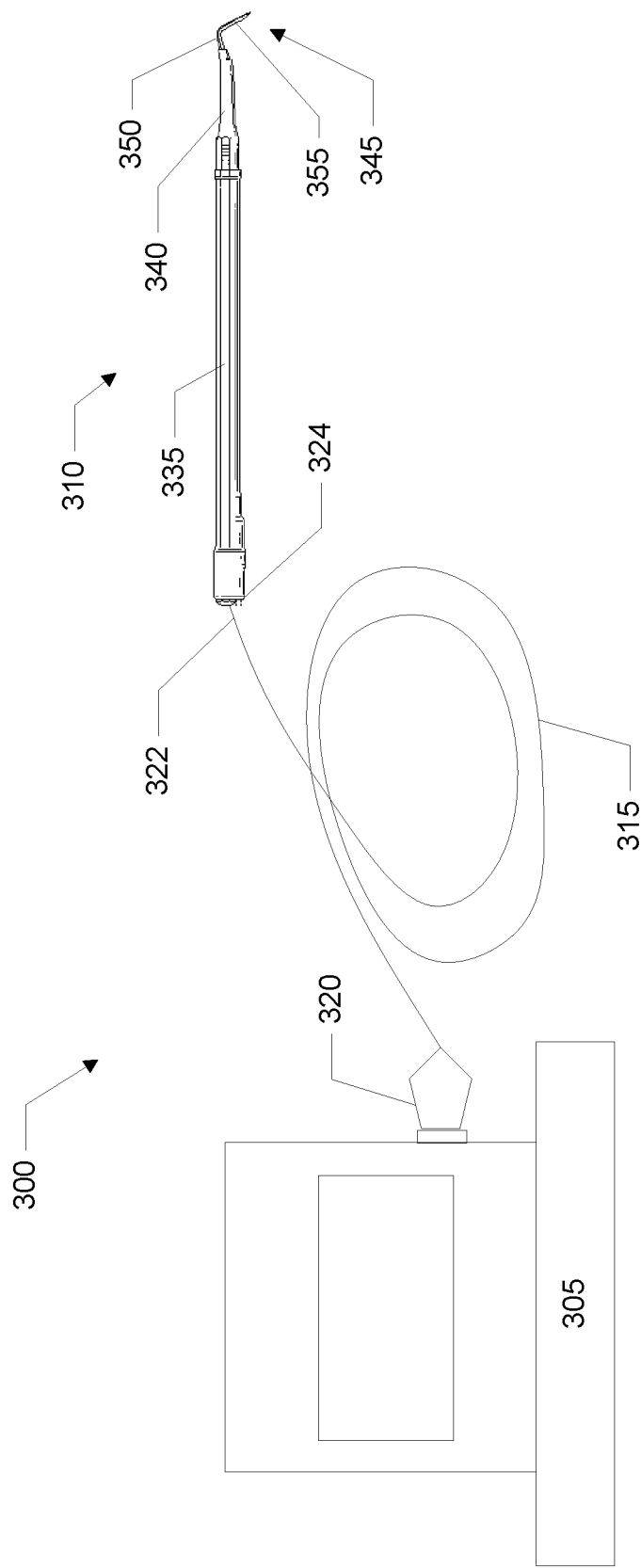
FIG. 3 shows a system of the invention including a monitoring console, a tissue elevator oximeter, and a cable connecting the elevator to the monitoring console.

FIG. 3 shows a system 300 of the invention including a monitoring console 305, a surgical elevator oximeter 310, and a cable 315 connecting the surgical elevator oximeter to the monitoring console. A connector 320 at a proximal end of the cable connects to the monitoring console.

In a specific embodiment, connectors are instead or additionally, included at a distal end 322 of the cable and at a proximal end 324 of the handle. These connectors allow the surgical elevator oximeter to be disconnected from the cable. However, these connectors are optional and are not included in some implementations.

The surgical elevator oximeter includes a handle 335, a shaft 340 connected to the handle, and a tip, probe, or blade 345 connected to an end of the shaft. The tip includes a second blade portion 350, a first blade portion 355, and one or more optical fibers in a resin. In a specific implementation, the tip may also include a sensor unit.

The length of the cable may vary. In a specific implementation, the length of the cable ranges from about 1.2 meters to about 3 meters. For example, the cable may be about 1.3, 1.4, 1.5, 1.6, 1.7, 1.8, 1.9, 2, 2.1, 2.2, 2.3, 2.4, or 2.5 meters long or greater. Depending on the specific application, the cable length may be less than 1.2 meters. In some applications, the cable length will be greater than 3 meters.

A specific application of the invention is operating room use or other places where it is desirable to maintain cleanliness and sterile conditions, such as isolation units. Patients in isolation units may have contagious diseases or compromised immune systems. Hospitals need to ensure that patients with a contagious disease do not infect others. Items introduced near the patient must either be disposed after use or properly cleaned. Hospitals also need to protect patients with compromised immune systems from sources of microorganisms. In these cases, a longer cable length, such as greater than 1.2 meters, is advantageous because this helps to separate the patient from sources of contamination, such as the console. Similarly, a longer cable length also minimizes contamination, such as contamination of the console, by the patient.

In a specific embodiment, the surgical elevator oximeter, entire length of cable, and connectors are packaged as a probe unit in a sterile package. The probe unit is detachable from the console after use and may be disposed. A user may then open a new sterile package containing a new probe unit. The package may be opened at the time of actual use or near the time of actual use so as to not contaminate the probe unit. The user can then connect this new and sterile probe unit to the console to begin monitoring. This disposable feature provides an additional level of protection in maintaining a sterile field around the patient.

In another embodiment, the sensor unit, entire length of cable, connectors, or combinations of these are detachable from the surgical elevator oximeter. The sensor unit, entire length of cable, connectors, or combinations of these may be packaged as a probe unit in a sterile package. After use, such as after spinal surgery, the user may detach the sensor unit and cable from the surgical elevator oximeter for disposal. The user may then open a new sterile package containing a new probe unit. The user can then attach the new sensor unit, cable, or both to the surgical elevator oximeter for future use.

In yet another embodiment, the elevator is permanently connected to the console via the cable. In this specific embodiment, a cover, sheath, cot, or other sterile drape may be placed over the tip to isolate the tip from the sterile surgical region and prevent contamination. The cover may be designed as a single use cover and be disposable after use. The cover may be translucent. This allows light from the tip or sensor unit to be transmitted through the cover and into the target tissue. A translucent cover also allows light from the target tissue to be transmitted through the cover and into the tip or sensor unit.

Typically, the cover is flexible so that it can conform to the shape of the tip. The cover may be made of any material suitable for use in surgery. For example, the cover may be made of plastic, silicon, rubber, neoprene, latex, polyethylene, and the like.

Short cables pose a problem. Short cables bring whatever element they are connected to within close proximity to the patient. Doctors and nurses must then devote additional care and time to ensure a sterile field around the patient. This may include, for example, additional cleansing of the elements before and after introduction to the sterile field, or sterile drapes on the elements.

In a specific embodiment, there may be other connectors on the cable instead of, or in addition to connector 320. These other connectors allow the cable to be separated into two or more pieces, allow additional lengths of cable to be attached, or both.

These additional connectors provide several benefits. For example, the cable attached to the surgical elevator oximeter can be disposed along with the surgical elevator oximeter after use. The cables attached to the console can be reused. Thus, the cable more likely to be contaminated, i.e., the cable attached to the surgical elevator oximeter, can be disposed. The cable less likely to be contaminated, i.e., the cable attached to the console can be reused. As another example, the connectors may be used to attach additional lengths of cable to extend the overall length of the cable.

In an implementation, the cable includes one or more optical wave guides enclosed in a flexible cable jacket. The optical wave guides may be used to transmit light from the console, through the surgical elevator oximeter and out openings in the tip and into the tissue. The optical wave guides may also be used to transmit the light received from the tissue back to the console.

The optical wave guides may have the shape of a polygon, such as a square, rectangle, triangle, or other shape. In other cases, the optical wave guides may have circular or oval shapes. In a specific implementation, the optical wave guides are multiple strands of fiber optic cable. The flexible cable jacket may be thin-walled PVC with or without an aluminum helical monocoil, shrink wrap tubing, plastic, rubber, or vinyl.

In a specific embodiment, all of the fiber optic cables are enclosed within one end, or both ends of the flexible cable jacket. Minimizing the number of exposed cables lowers the likelihood that the cables will get entangled. In another embodiment, the fiber optic cables are not enclosed together and instead each fiber optic cable is enclosed in its own flexible cable jacket.

In a specific implementation, the cable is passive. For example, it will not contain any active, generative properties to maintain signal integrity. However, in other implementations, the cable may include active components. The cable may include active components to amplify the signal transmitted through the sensor unit, received at the sensor unit, or both. For example, long lengths of cable subject to significant attenuation may require amplification. Amplification may also be required if the monitored site contains a particularly dense structure such as bone.

In a further embodiment, the cable may include both fiber optic cable and electrical wiring. For example, one or more ends of fiber optic cable to emit light into the tissue may be coupled to the tip. Photodetectors may also be coupled to the tip receive light transmitted from the tissue. Thus, in this specific embodiment the cable may include fiber optic cable to transmit light from the console to the tip and electrical wiring to transmit signals received by the photodetectors back to the console.

As another example, the radiation sources such as light emitting diodes (LEDs) may be coupled to the tip. One or more ends of fiber optic cable may be coupled to the tip to transmit the light received from the tissue back to photodetectors in the console. Thus, the cable may include electrical wiring to transmit power to the LEDs and fiber optic cable to receive light transmitted from the tissue.

In an embodiment of the invention, each opening on the sensor unit and corresponding cable is dedicated to a particular purpose. For example, a first opening on the sensor unit (and corresponding fiber optic cable) is dedicated to transmitting light from the monitoring console. A second opening on the sensor unit is dedicated to transmitting a signal received at the second opening to the monitoring console.

Some embodiments use a particular opening and cable for multiple purposes (e.g., both input and output) using a scheme such as multiplexing.

In a specific embodiment, a particular opening and cable transmits an output to affect a reaction (e.g., sending electrical signals to stimulate muscle or other tissue). Another opening and cable transmits the resultant signal back to the monitoring device. In yet another embodiment, the openings and cables may simply detect changes and transmit these changes back to the monitoring device. For example, the openings and cables may carry voltage changes in the patient's skin back to the monitoring device.

In an implementation, the connectors on the cable, monitoring console, surgical elevator oximeter, and combinations of these have indicators. The indicators may be color indicators that are painted on, or raised indicators, or both. These indicators help the user to properly attach the cable to the monitoring console, surgical elevator oximeter, or both. For example, the indicators may include green arrows placed on the cable connectors, monitoring console, and surgical elevator oximeter. Alignment of the arrows indicates proper attachment of the cables. Further, there may be instructions printed on the console, cable, and surgical elevator oximeter that instruct the user on the proper attachment of the cable.

Connector 320 attaches to the monitoring console. The connector protects the cable from accidental disconnection. The connector may be a threaded collar on a cable end that threads onto the monitoring console. Alternatively, the connector may be a lug closure, press-fit, or snap-fit.

In an implementation, the console is portable. Thus, the console can be hand-carried or mounted to an intravenous (IV) pole. A portable console can follow a patient anywhere in the hospital, eliminating the need to change connections whenever a patient is moved. Moreover, a portable design facilitates use and assessments in numerous other locations besides a hospital.

A portable console is typically battery-operated. The battery is typically a rechargeable type, such as having nickel cadmium (NiCd), nickel metal hydride (NiMH), lithium ion (Li-Ion), lithium polymer, lead acid, or another rechargeable battery chemistry. The system can operate for a certain amount of time on a single battery charge. After the battery is drained, it may be recharged and then used again.

The portable console may also have a power-saving feature. This reduces battery consumption during continuous measurements. The power-saving feature may, for example, darken the console's display screen after a certain time of inactivity. The time may be approximately five, ten, fifteen, or twenty minutes. Alternatively, the user may program the time.

The console may include a power management circuit. When the power management circuit detects a low battery condition, the power management circuit may cause a warning to show on the display. The power management circuit may include other features as well. For example, when the power management circuit detects a low battery condition (e.g., voltage drops below a threshold value), the power management circuit may cause the system to power down after a specified amount of time. The specified amount of time may be programmed by the user. As another example, when the power management circuit detects a low battery condition, and the system is in an off mode and AC input is not connected to the power source, the power management circuit will not permit the system to be powered to an on mode.

In a specific implementation, the portable console weighs approximately 4.3 kilograms. However, the weight may vary from about 3 kilograms to about 7 kilograms including, for example, 3.5, 4, 4.5, 5, 5.5, 6, 6.5, 7, or more than 7 kilograms.

In another implementation, the console is not hand-held or portable. The console may be a large, nonportable device that is attached to a wall or secured to a stand or surface. In this implementation, the system is typically connected to AC power. A battery may be used as a back-up to the AC power.

In a specific implementation, the console provides alerts. The alerts may be visual (e.g., a flashing light on a display of the console), audible, or both. Visual alerts may be designed so that they are viewable from any location (e.g., a flashing light on the top of the console). In a chaotic and noisy situation, this allows users to quickly respond to a patient. These alerts may signal a problem with the system. This includes, for example, insufficient signal strength, kinks or sharp bends in the cable, debris on the sensor unit, debris on a coupling surface between the cable and the console, insufficient electrical power, a low battery, an improperly attached cable, or other problem.

An alert may also signal when the system is ready for patient monitoring. The alerts may also provide warnings at certain oxygen saturation levels. For example, if the oxygen saturation level or other critical measurement falls below a threshold value then the system will provide an alert. In a specific embodiment, the alert is provided by the console. However, the alert may also be provided by the surgical elevator. For example, the surgical elevator may include warning lights. Such warning lights may be placed on the handle, shaft, or both. This allows the user to see, for example, whether the oxygen saturation level of the tissue being elevated has fallen below a threshold level, without having to turn and look at the console. Different alerts may be used depending on the type of problem detected by the system. Different alerts include different colors, sounds, and intensities of colors and sounds.

The console may provide an alert when the sensor unit is placed in a suitable location for a measurement. The alert may vary in intensity depending on the suitability of the location. The alert may be audible, or visual, or both. An audible alert allows the user to determine the suitability of a location without having to look away from the patient.

The alerts may be user-programmable. That is, users may set which alerts are enabled, the threshold at which they are activated, and the intensities of the alerts. For example, a user may decide to enable the oxygen saturation alert, set the alert to occur if and when the oxygen saturation level falls below a certain value, and set the volume level of the alert.

The console may also include a mass storage device to store data. Mass storage devices may include mass disk drives, floppy disks, magnetic disks, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, oxygen saturation measurements and the time and date measured. The oxygen saturation measurements may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

A screen on the console displays the patient's data, such as an oxygen saturation measurement. The screen may be a flat panel display such as a liquid crystal display (LCD), plasma display, thin film transistor liquid crystal display (TFT LCD), electro-luminescent (EL), or organic light emitting diode (OLED) display. The screen may include a touch screen interface. Such touch screen interfaces are easier to clean compared to keypads if they become contaminated because they do not contain mechanical parts.

The screen may display numbers, text, graphics, and graphical trends in color. Different colors may correspond to different measurements or threshold levels. The text and numbers may be displayed in specific languages such as English, Spanish, French, Japanese, or Tagalog. The displayed language is user-programmable.

In a specific implementation, the screen displays data related to a single regional oxygen saturation reading. For example, this may include a single plot or graph.

Users can also vary the size of the displayed information on the console's screen. This allows the display to be viewed at a distance, increases the viewing angle, and allows users with vision limitations to see the information.

The console, in addition to the display, may also include a processor, signal emitter circuit, signal detector circuit, and a receptacle to removeably couple ends of one or more optical fibers. In a specific implementation, the ends of one or more optical fibers are instead permanently connected to the console. The signal emitter circuit may operate to send a signal through the one or more optical fibers. The signal detector circuit then receives a signal via one or more optical fibers.

In a specific implementation, the console includes a first radiation source and a second radiation source. The radiation sources may be dual wavelength light sources. In other words, first radiation source provides two wavelengths of radiation and second radiation source provides two wavelengths of radiation. First radiation source, second radiation source, or both may include one or more laser diodes or light emitting diodes (LEDs) that produce light in any wavelength, but typically the wavelengths range from about 600 nanometers to about 900 nanometers. In a specific implementation a first wavelength of light is generated that has a wavelength of about 690 nanometers. A second wavelength of light is generated that has a wavelength of about 830 nanometers.

In a specific implementation, the signal emitter circuit may include one or more laser emitters, light emitting diode (LED) emitters, or both. The signal emitter circuit may be used to generate an optical signal having two or more different wavelengths to be transmitted through the sensor unit. The wavelengths may range from about 600 nanometers to about 900 nanometers.

In yet another embodiment, light may be transmitted through one or more filters in order to produce the desired wavelength of light. For example, white light which includes all the colors of the visible light spectrum may be transmitted into the tissue via, for example, a white LED. A filter (e.g., colored filter) located at the tip or in the console may be placed over an end of fiber optic cable in order to filter out the unwanted wavelengths of light. As another example, the white light, prior to being transmitted into the tissue, may pass through a filter to produce the desired wavelength of light to transmit into the tissue.

In a specific implementation, one or more near-infrared radiation sources are included within the console. In other implementations, the radiation sources may be external to the console. For example, the radiation sources may be contained within a separate unit between the console and sensor unit. The radiation sources may, for example, be contained in the handle of the surgical elevator oximeter. In yet another implementation, some radiation sources may be within the console while other radiation sources are external to the console.

These radiation sources may be near-infrared lasers. In a specific implementation, there is one near-infrared laser located within the console. In other implementations, there may be more than one near-infrared laser. For example, there may be 2, 3, 4, 5, 6, 7, 8, 9, 10, or more than 10 radiation sources. These radiation sources may generate approximately 30 milliwatts of power. However, the power can range from about 20 milliwatts to about 100 milliwatts of power or more. Depending on the application, the power may be less than 20 milliwatts.

Also, only a percentage of the power output of the source is transmitted to the tissue. For example, when the laser diode output is 30 milliwatts, the power that gets to the tissue will be about 3 milliwatts. So, approximately 1/10 of the power of the laser diode is transmitted into the tissue.

In a specific implementation, a single pulse of light is transmitted into the tissue. In another implementation, multiple pulses of light may be transmitted into the tissue. For example, a first pulse of light may be received by a first detector. A second pulse of light may be received by a second detector.

This application describes aspects of the invention in connection with a handheld elevator tool or probe. However, the principles of the invention are also applicable to an elevator tool or other tool with oximeter sensor when implemented in an endoscopic instrument. Endoscopy is a minimally invasive diagnostic medical procedure that is used to assess the interior surfaces of an organ by inserting a tube into the body. At the end of the endoscope tool is an elevator or other blade or tool as described in this application.

The endoscopic instrument with elevator or other tool with oximeter sensor at the end can have a robotic interface. The robotic interface allows a doctor control the instrument from a remote location. For example, the doctor in New York City can use a tool of the invention to perform a remote procedure on a patient who is located in Barrows, Alaska. The doctor will be able to make oxygen saturation measurement using the elevator or other tool. The robotic interface may have a haptic interface which provide feedback to the doctor, or may not have a haptic interface. When a haptic interface for the tool is not available, the readings provided by the tool may give the doctor an indication of the condition of a tissue.

Figure 4:
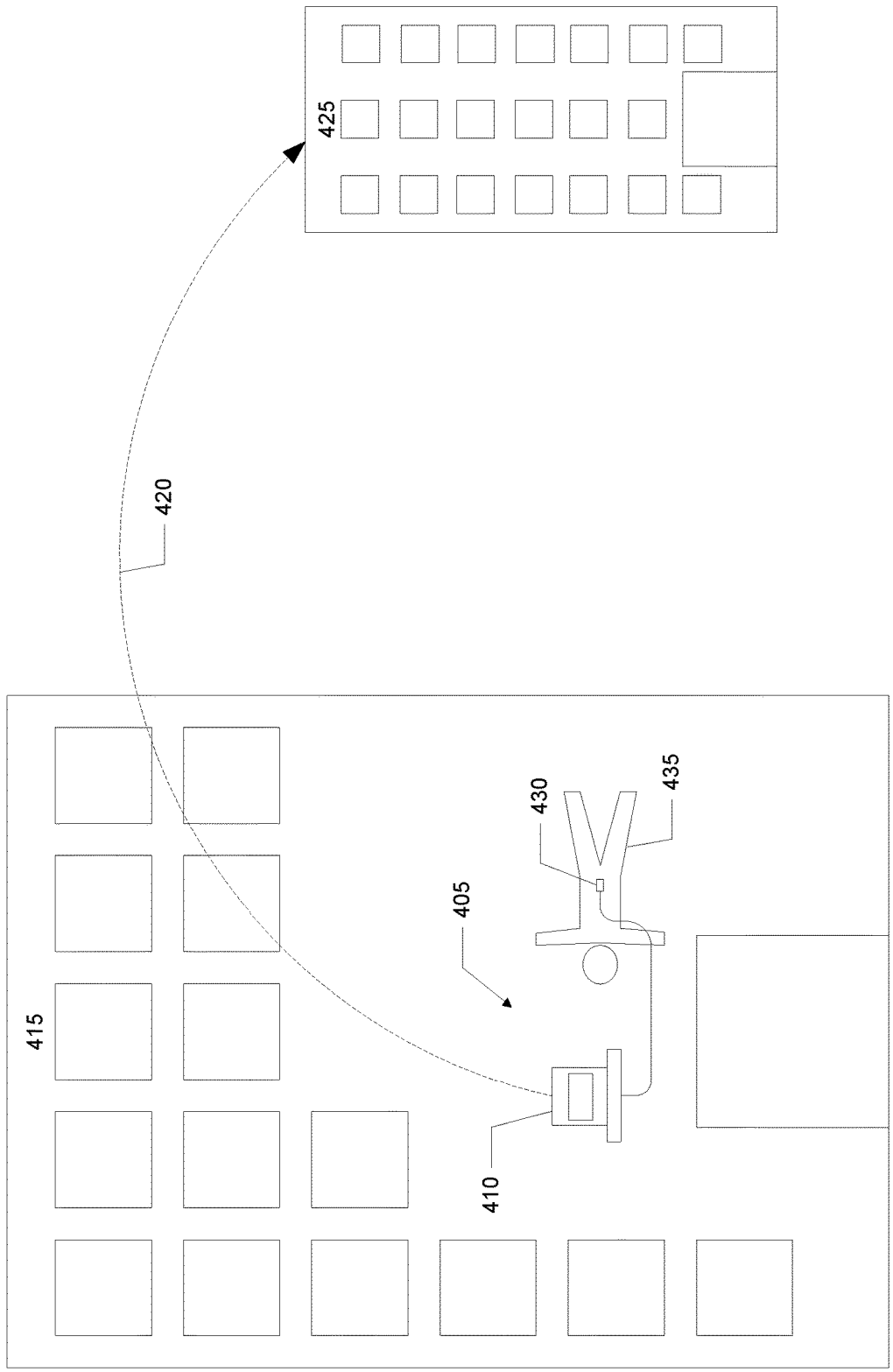
FIG. 4 shows an example of a wireless implementation of the invention.

FIG. 4 shows an example of a wireless implementation of the invention. A system 405 includes a monitoring console 410 at a field location 415 which transmits 420 the patient's data to a receiving location 425. The figure shows the monitoring console transmitting the data, using for example, a modem in the monitoring console. However, in another implementation, a surgical elevator 430 may wirelessly transmit the data the receiving location.

In the figure, the field location is in an operating room and a patient 435 is undergoing spinal surgery, such as spinal disk surgery. In other implementations, the field location may be a trailer, a tent, or in a vehicle such as a car, ambulance, automobile, truck, bus, train, plane, boat, ship, submarine, or helicopter. The field location may also be on a battlefield.

The receiving location also varies. The receiving location may be a hospital, clinic, trauma center, physician's home or office, or a nurse's home or office. The monitoring console or sensor unit may also transmit to multiple receiving locations. For example, data may be transmitted to both the hospital and the physician's home.

A variety of devices may receive the data. This includes, for example, a monitoring console, other monitoring stations, mobile devices (e.g., phones, pagers, personal digital assistants (PDAs), and laptops), or computers, or combinations of these.

The distance between the field and receiving location may vary. The field and receiving location could be in different countries, states, cities, area codes, counties, or zip codes. In other cases, the field location and receiving location may be in different parts of the same room or in different rooms in the same building.

The wireless transmission may be analog or digital. Although FIG. 4 shows the system transmitting data directly to the receiving location, this is not always the case. The system may relay data to the receiving location using intermediaries. For example, satellites may rebroadcast a transmission. While in one embodiment, a communication network is the Internet, in other embodiments, the communication network may be any suitable communication network including a local area network (LAN), a wide area network (WAN), a wireless network, an intranet, a private network, a dedicated network, phone lines, cellular networks, a public network, a switched network, and combinations of these and the like. Wireless technologies that the system may employ include: Wi-Fi, 802.11a, 802.11b, 802.11g, 802.11n, or Bluetooth, or combinations of these and the like. The system also has the ability to switch from one communication technique to another if, for example, the current network is unreliable or there is interference. The switch may either be automatic or manual.

The system's ability to wirelessly transmit data offers several advantages. For example, data received by the monitoring console may be wirelessly transmitted to the receiving location where the patient's medical records may be stored. The data may then be saved as part of the patient's medical history.

Figure 5:
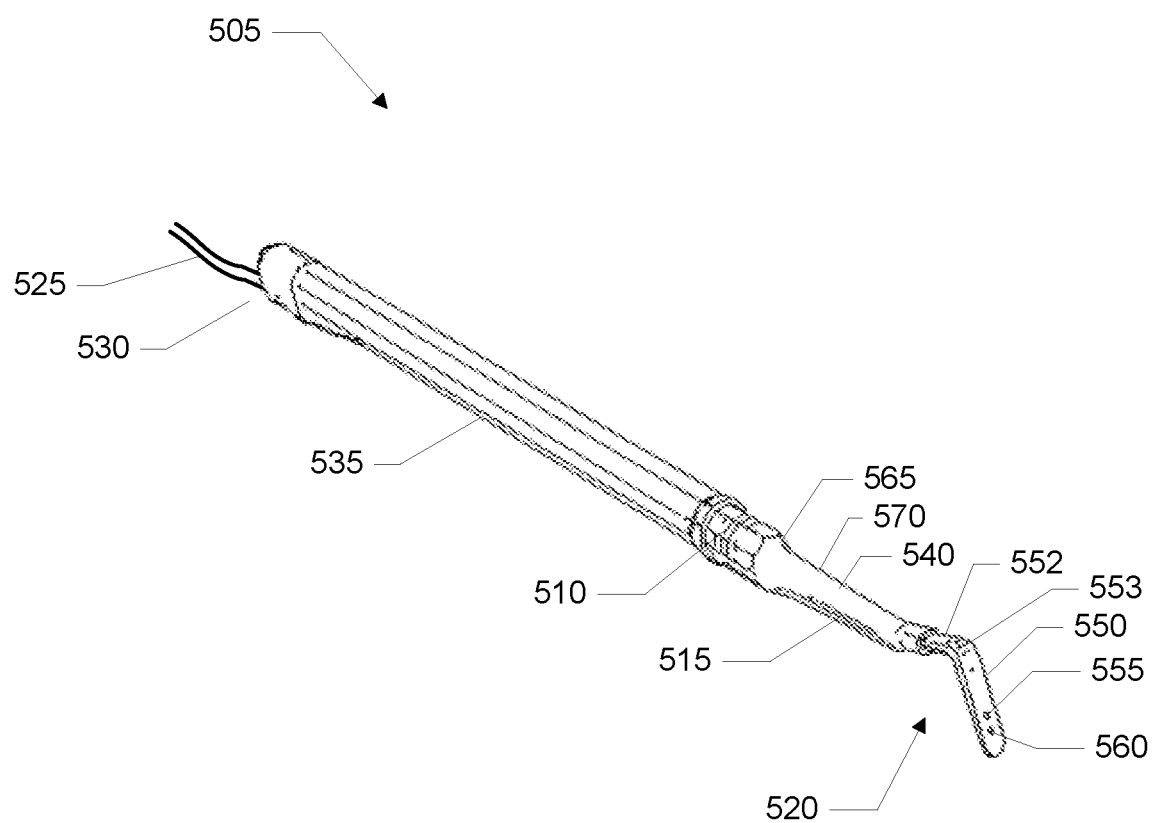
FIG. 5 shows a perspective of a tissue elevator oximeter.

FIG. 5 shows a perspective view of a surgical elevator 505. The surgical elevator includes a handle 510, connected to a shaft 515, connected to a tip 520. A cable 525 exits at a proximal end 530 of the handle. The handle may be at least partially enclosed by a handle jacket 535. The shaft may be at least partially enclosed by a shaft jacket 540. The tip includes a first blade portion 550 that is connected to a second blade portion 552 at a connection 553. In a specific embodiment, the first blade portion includes two openings including openings 555 and 560.

Typically, connection 553 has rounded edges or corners. In a specific embodiment, most, if not all, edges and corners of the elevator are curved, rounded, or blunted. These features help to avoid contact injury to the nerve and other tissues surrounding the nerve. However, depending on the application, some embodiments of the invention may include one or more sharpened edges on the elevator. Such an elevator may be designed for the cutting of tissue.

The surgical elevator including the handle, shaft, and tip may be made of any material suitable for use in surgery, especially for human surgery. Generally, a material is suitable for surgery as long as it is not toxic or reactive (e.g., causing an allergy or undesirable chemical reaction) for a particular person, organism, or procedure.

Further, in a specific implementation, the material of the surgical elevator is not reflective or minimally reflective. This will ensure that more of the light which is transmitted into the tissue is received back at the detectors, instead of being reflected off the elevator. For example, the elevator may be coated with an antireflective material (such as a black oxide coating) to make it less reflective than the original starting material. Or the elevator may be processed (e.g., bluing, anodizing, or oxidizing) to make the surface less reflective than the original starting material. The elevator may be colored (e.g., black flat color), or finished (e.g., matte finish), or textured (e.g., bead-blasted finish) to reduce reflectivity. Another benefit of reducing reflectivity of the elevator is that there will be less glare for the surgeon when operating.

In another specific implementation, the material of the elevator is not electronically conductive or has reduced electrical conductivity compared to the original starting material. Because the elevator is inserted between tissues (e.g., nerve and other tissue) to ensure a threshold gap between the tissues it may not be desirable to shock the tissues (e.g., nerves) with electrostatic energy accidentally. The elevator may be made from material that is not conductive such as a ceramic, plastic, or resin. Or the elevator may include insulating material inserted between the tip (which touches the nerve) and the point at which the surgeon holds the elevator (or other portions of the elevator). For example, the handle may include rubber or the surgeon may wear nonconductive gloves, and this will stop accidental electrostatic discharges.

In another specific implementation, the material of the elevator is not thermally conductive or has reduced thermal conductivity compared to the original starting material. Because the elevator may contact nerves and other tissue, temperature changes in the elevator can be propagated to the nerve quite quickly. It is generally desirable not to thermally heat the nerve or else it may become damaged. So, the elevator may be made from material that is not thermally conductive such as a ceramic, plastic, or resin. Or the elevator may include thermally insulating material inserted between the tip (which touches the nerve) and other portions of the elevator.

In a specific embodiment, the elevator including the handle, shaft, and tip (e.g., first blade portion and second blade portion) are all made from the same material. The material may be metal, such as steel, stainless steel, or surgical stainless steel, or combinations of these and other suitable materials. Some other metals that may be used include gold, silver, rhodium, titanium, tungsten, molybdenum, and aluminum. The handle, shaft, and tip may be made of an alloy of two or more elements (e.g., iron, carbon, chromium, molybdenum, and nickel). In other embodiments, the handle, shaft, and tip may be made of plastics, ceramics, or composites (e.g., carbon fiber). The handle, shaft, and tip may also include a combination of materials such as steel surrounded by shrink-wrap tubing.

The shaft may include two sections including a shaft base 565 and a shaft stem 570. In the example shown in FIG. 5, the shaft base has the shape of a frustum which tapers into the shaft stem. That is, a diameter of the shaft base is greater than a diameter of the shaft stem. The shaft stem may also have the shape of a frustum which tapers into the tip.

In a specific embodiment, the slope of the shaft base is different from the slope of the shaft stem. For example, the slope of the shaft base may be shallower than the slope of the shaft stem as in the example shown in FIG. 5.

In a specific embodiment, the shaft is a solid rod, and one or more fiber optic cables (e.g., two fiber optic cables) are run along at least some portion of the length of the shaft. The ends of the fiber optic cable terminate at one or more openings in the tip so that light can be transmitted into the nerve (or other tissue) and received from the nerve. The opposite ends of the fiber optic cable may terminate at the connector on the cable, which will be connected to the console (see, e.g., FIG. 3). The shaft and fiber optic cables can be bound together using the shaft jacket which may include heat-shrink tubing.

Typically, the handle is an extended or elongated rigid member. The handle may be made of any material such as plastic, metal (e.g., steel, aluminum, and titanium), ceramics, composites (e.g., carbon fiber), or rubber, or combinations of these. The handle may be ergonomically designed so that it is comfortable for a user to hold. Some examples of ergonomic designs include easy to hold shapes, such as an octagon as shown in FIG. 5, the use of soft materials (e.g., rubber) as the handle jacket, and lightweight materials (e.g., titanium).

A specific embodiment may include counterbalance weights to balance the weight of the elevator between the tip and the proximal end of the handle. For example the handle may include a counterbalance weight at the proximal end of the handle in order to counter the weight of the tip.

The handle, handle jacket, or both may also be textured (e.g., knurled) so that the tool is less likely to slip from the user's hand.

In an embodiment, shaft jacket 540 includes an internal channel or passageway that runs the full length or some portion of the length of the shaft. The passageway may be used to contain optical wave guides, electrical wiring, or other wiring, or combinations of these.

In another embodiment, shaft 515 is hollow, including an internal channel or passageway that runs the full length or some portion of the length of the shaft. The passageway may extend into the handle. The passageway may be used to contain optical wave guides, electrical wiring, or other wiring, or combinations of these.

In a specific embodiment, the shaft and handle are molded as a single unit. In another embodiment, the shaft and handle are separate pieces. The shaft may extend through the full length of the handle. In yet another embodiment, the shaft extends only through a portion of the handle. The shaft may be secured to the handle using an adhesive, a threaded connection, a lug closure (e.g., twist and lock), a press fit, or combinations of these.

In a specific embodiment, the handle jacket and shaft jacket are made from the same material. The material may be, for example, heat-shrink tubing, thermoplastics (e.g., polyolefin, fluoropolymer, polyvinyl chloride, neoprene, and silicon elastomer), rubber, synthetic rubber, natural rubber, elastomer, fluoroelastomer, or combinations of these. In other implementations, the handle jacket and shaft jacket may be made from different materials. For example, the shaft jacket may be heat-shrink tubing while the handle jacket is synthetic rubber.

Figure 6:
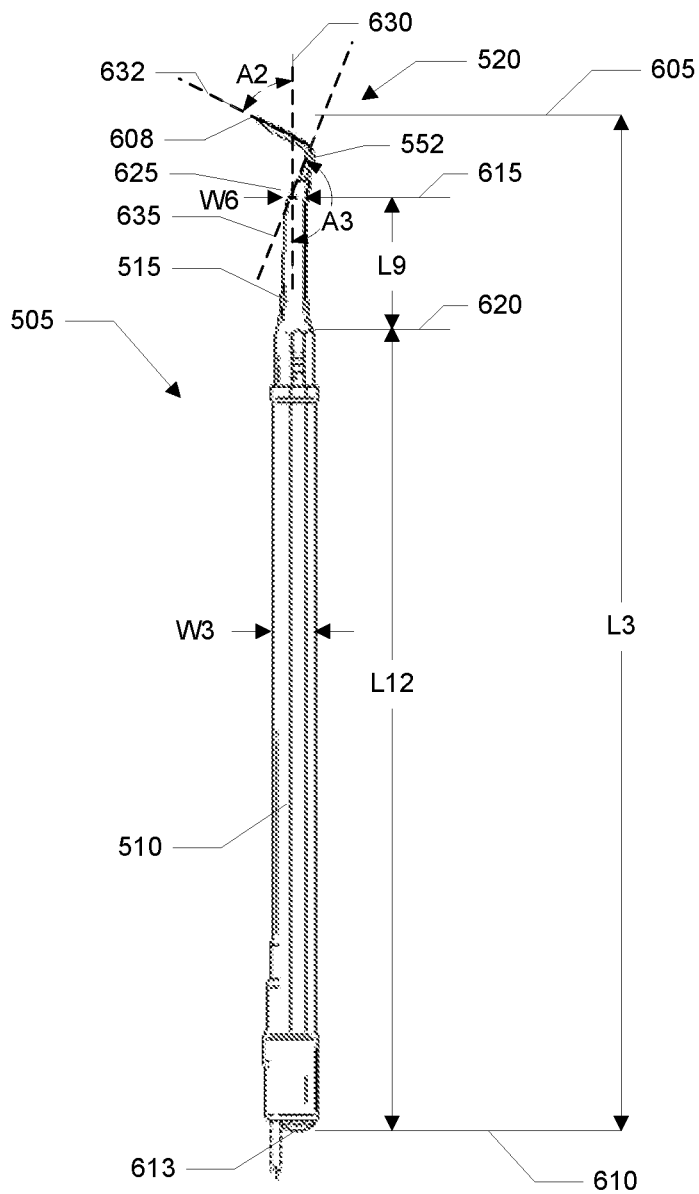
FIG. 6 shows a side view of the tissue elevator oximeter.

FIG. 6 shows a side view of surgical elevator oximeter 505. A distance L3 (i.e., elevator length) is between a line 605 at a distal end 608 of the elevator and a line 610 at a proximal end 613 of the elevator. A distance L9 (i.e., shaft length) is between a line 615 and a line 620. A distance L12 (i.e., handle length) is between line 620 and line 610.

A distance W3 indicates a width of the handle. For example, in a specific implementation including a handle having a cross section in the shape of a regular octagon, the width is the longest diagonal of the octagon. In another implementation including a handle having a cross section in the shape of a circle, the width is the diameter of the circle. A distance W6 indicates a width of the shaft at a distal end 625 of the shaft where the tip is connected.

In a specific embodiment, a portion of the tip (i.e., second blade portion) initially projects away from an axis 630 which passes longitudinally through the shaft and handle. The tip (i.e., first blade portion) then bends towards axis 630. In a specific implementation, the first blade portion passes through axis 630 as shown in the example in FIG. 6. In other implementations, the first blade portion terminates before reaching axis 630.

In an embodiment, the openings on the first blade portion are aligned with the handle. That is, a line 632 passing through the openings intersects axis 630. Line 632 and axis 630 may form an angle A2. Typically, angle A2 is an acute angle, i.e., an angle that is less than 90 degrees. In a specific embodiment, angle A2 is about 63 degrees, but may range from about 45 degrees to about 90 degrees, including 50, 55, 60, 65, 70, 75, 80, 85, more than 85 degrees, and less than 45 degrees.

In an embodiment, second blade portion 552 of tip 520 is at an angle relative to shaft 515. For example, an axis 635 passes longitudinally through the second blade portion. Axes 630 and 635 form an angle A3. In a specific embodiment, angle A3 is about 160 degrees, but may range from about 135 degrees to about 180 degrees. This includes, for example, 135, 140, 145, 150, 155, 160, 165, 170, 175, 180, more than 180 degrees, and less than 135 degrees.

The various angles of A2 and A3 allow the user to select that angle that the user is most comfortable working with. That is, users differ in their techniques and preferences. The range of angles thus accommodates various users' preferences. In other implementations, the shaft, tip, or both may be bendable by the user who can then shape the shaft or tip into any angle or configuration. In yet another implementation, the shaft may include two or more pieces that are pivotly connected such as via screws and nuts. This too allows the user to determine and set the desired angle and configuration.

Several dimensions for the elevator are shown in table A below.

TABLE A

| Dimension | First Implementation (millimeters) | Second Implementation (millimeters) | Third Implementation (millimeters) | Range of Dimensions (millimeters) |
|---|---|---|---|---|
| Elevator length (L3) | 175 | 210 | 140 | 130-227 |
| Shaft length (L9) | 126 | 151 | 100 | 94-164 |
| Handle length (L12) | 128 | 154 | 102 | 96-166 |
| Handle width (W3) | 8 | 10 | 6 | 5-11 |
| Shaft width (W6) | 3 | 4 | 2 | 1.75-5 |

Although some specific dimensions, angles, and geometries, and elevator blades are shown and described in this application, one of skill in the art would understand that an elevator blade may be dimensioned or angled differently, so as to provide the appropriate control for a user (e.g., a surgeon) of the elevator and also as appropriate for the specific nerve or tissue being operated on. Further, the elevator may be adjustable such as having a variable length blade or a pivotable angle blade, or a variable length shaft or handle.

In a specific embodiment, the shaft and handle may be detached and reattached by the user. For example, the shaft may be screwed into the handle. In another embodiment, the tip and shaft may be detached and reattached by the user. For example, the tip may be screwed into the shaft.

Separating elevator into two or more pieces (e.g., handle, shaft, and tip) that may be detached and reattached by the user has several benefits. For example, the user may select a tip having the specific dimensions (e.g., length, width, thickness, and angles) that are appropriate for the application and use the same handle without having to purchase a new elevator. As another example, a specific implementation may include disposable tips. That is, after use, the user may detach the tip from the shaft (e.g., unscrew tip from shaft), open a sterile package containing a new tip, and attach the new tip to the shaft (e.g., screw new tip onto shaft).

Figure 7:
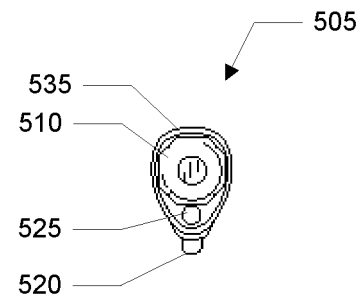
FIG. 7 shows a view of the proximal end of the elevator looking towards the distal end.

FIG. 7 shows a view of surgical elevator oximeter 505 at the proximal end and looking towards the distal end. In a specific implementation, handle 510 and cable 525 are at least partially enclosed by handle jacket 535.

In the example shown in FIG. 7, the cable is positioned outside of the handle. In another embodiment, the cable may be positioned at least partially within the handle. For example, the handle may be hollow and include a cavity, lumen, or channel through which the cable runs. In this specific implementation, the handle jacket may be omitted because the cable is unlikely to become tangled.

In yet another embodiment, the handle may include a groove into which the cable is at least partially recessed. An adhesive (e.g., epoxy) may be used to secure the cable in the groove.

In the example shown in FIG. 7, the handle jacket secures the cable to the handle so that the cable does not become tangled. In another embodiment, the cable may be secured to the handle using other fasteners and other fastening methods. For example, the cable may be secured to the handle with, for example, an adhesive (e.g., epoxy), tape, straps, or bands.

Although the example shown in FIG. 7 shows the cable positioned on a bottom side of the handle, this may not be the case in other embodiments. For example, the cable may be positioned on a side of the handle (e.g., right-hand side, left-hand side) or on the top of the handle.

In a specific implementation, the handle has the cross-sectional shape of an octagon as shown in FIG. 7. However, it should be appreciated that in various other embodiments, the cross-sectional shape of the handle may include a different shape. For example, the cross section may have a different polygonal shape including regular and irregular polygons.

A regular polygon is a polygon where all the sides have the same lengths and all the interior angles are the same. An irregular polygon is a polygon where at least one side has a different length than another side or where at least one interior angle is different from another interior angle. Some examples of polygons include squares, rectangles, triangles, trapezoids, pentagons, and hexagons.

One benefit of using a polygonal cross section (e.g., octagon) is that the shape includes multiple sides or facets (e.g., eight sides or facets in the case of an octagon) which offer a variety of positions in which the user may hold the elevator. For example, depending on the application, the user may rotate the elevator about a longitudinal axis passing through the handle while probing the surgical site and still be able to securely grip two or more sides of the elevator.

In yet another embodiment, the cross section may include shapes having one or more curved edges, including convex edges and concave edges. Some examples of shapes with curved edges include circles, ovals, crescents, and ellipses. These features may be used to make the elevator comfortable and easy to hold.

In still another embodiment, the cross-sectional shape of the handle may vary. For example, the cross-sectional shape at the proximal end of the handle may be an octagon as shown, while the cross-sectional shape at the distal end of the handle may be a circle.

Figure 8:
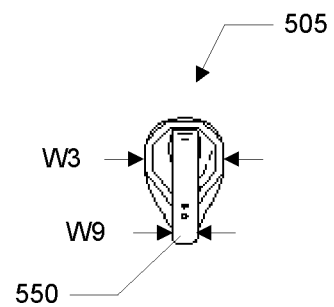
FIG. 8 shows a view of the distal end of the elevator looking towards the proximal end.

FIG. 8 shows a view of surgical elevator oximeter 505 at the distal end and looking towards the proximal end. A distance W9 indicates the width of the first blade portion.

Typically, the width of the first blade portion is less than the width of the handle (W3). For example, the width of the first blade portion may be two, three, four, or more than four times less than the width of the handle. In a specific embodiment, width W9 is about 3 millimeters, but may range from about 0.5 millimeters to about 10 millimeters.

Generally, a wide handle reduces hand fatigue and allows the user to control the elevator while a narrow blade allows the user to insert the blade into small areas. However, depending upon the application, the width of the first blade portion may be greater than the width of the handle.

FIG. 9 shows a top view of surgical elevator oximeter 505. FIG. 10 shows a bottom view of surgical oximeter 505.

FIG. 11 shows a perspective view of a first embodiment of a tip 1105 which is coupled to a shaft 1106. The tip includes a first blade portion 1110 having a proximal end 1112 which is coupled to distal end 1114 of a second blade portion 1116. The first blade portion has a first surface portion 1126. A second surface portion 1129 is opposite the first surface portion. The second blade portion has a third surface portion 1132. A fourth surface portion 1135 is opposite the third surface portion.

In a specific embodiment, the tip includes two openings including openings 1123b and 1123b on first surface portion 1126. Opening 1123a may include a source structure and opening 1123b may include a detector structure. In another embodiment, opening 1123a may instead include the detector structure and opening 1123b may instead include the source structure.

Although this example shows two openings (i.e., 1123a and 1123b), other embodiments may have more than two openings, or less than two openings. There may be one, two, three, four, five, six, seven, eight, or more than eight openings.

In a specific embodiment, one or more of the openings are visible or unconcealed on the first surface portion. For example, the openings may be unobstructed. As another example, the openings, though still unconcealed, may be covered by a translucent film or layer (e.g., thin film of polyurethane). The translucent film may help to protect the source and detector structures from becoming contaminated, but still allow light or radiation to pass through.

In an implementation, one unconcealed opening provides a source of radiation and another unconcealed opening provides a detector of radiation. These unconcealed openings can be completely exposed, uncovered, or unblocked.

Or the unconcealed openings may be protected or covered by layer or film which is invisible to the radiation which is being emitted or detected.

The radiation can be visible light, but may also be radiation not in the visible region of the electromagnetic spectrum. The unconcealed openings permit the transmission and reception of radiation which is being used to make measurements.

For example, radiation can be transmitted from a source diode through an optical fiber through the source opening to tissue. Optionally, the source opening may be covered by a coating, which still allows this radiation to pass through. Similarly, the detector opening can also have such a coating (or not). And the received radiation is received at the opening and transmitted through an optical fiber to a photodetector.

Furthermore, a specific embodiment may not have any openings. For example, the source structure, detector structure, or both may be located outside a perimeter of the tip. As an example, the source structure, detector structure, or both may be coupled to a side of the tip. In a specific embodiment, the source structure, detector structure, or both are connected to one or more notches on a side of the tip. For example, a first notch on a side of the tip may include the source structure. A second notch on the opposite side of the tip may include the detector structure. In another embodiment, the notches (e.g., first and second notches) may be on the same side of the tip. As another example, the tip or a portion of the tip may be constructed of a translucent material, such as clear plastic. Light from a source structure may then pass through the translucent material, into the tissue, and then be received by a detector structure as the light passes back through the translucent material.

In another embodiment, one or more components are mounted on a surface (e.g., 1126) of the tip. The components include radiation sources, photodetectors, or circuitry (e.g., a circuit board), or any combination of these. For example, the radiation source is a surface-mounted LED chip.

In an implementation, there are two radiation sources (e.g., LEDs), one for red light and the other for infrared light. There is one photodectector. For example, in various implementations, one radiation source is mounted on the tip surface. Two radiation sources are mounted on the tip surface. A photodetector is mounted on the tip surface. A radiation source (or two radiation sources) and photodetector is mounted on the tip surface. Typically, a component is held in place by solder or an adhesive.

Furthermore, the surface can have a cavity to hold one or more of the components. Depending on a depth of the cavity, the component can be flush with the surface.

An epoxy or resin can be used to cover a component, but this is not necessary. Further, a translucent film (e.g., thin film of polyurethane) can be used to provide a biocompatible barrier to prevent contact between the electronic components and the tissue.

The components are connected to the console using wires (e.g., electrical wires). The wires can run through an internal channel in the blade to the handle. This channel will run approximately parallel to a surface of the blade. Or, the wires can run from the component, through an opening in the blade, to the other side of the blade, and along the other side of the side to the handle. Such openings will be approximately transverse to a surface of the blade.

An epoxy or resin can be used to cover the wires on the other side of the blade, but this is not necessary. For example, the wires can be run in a ribbon or cable that is attached to the other side of the blade.

In another embodiment, one or more of the components are mounted to a circuit board, which is in turn mounted to first surface portion 1126 of the blade. The circuit board can be a thin-film circuit board or a flexible circuit board. For example, each radiation source can be on a separate circuit board, or there can be multiple radiation sources on a single circuit board. There can be one or more radiation sources on the same circuit board with a photodetector.

In various implementations of a device, components can be mounted at the tip or in the console (e.g., connected via optical fiber). A device may include any combination of some components mounted at the tip, while others are at the console. For example, a radiation source can be mounted at the tip, while a photodetector is in the console. The radiation source can be in the console, while the photodetector is mounted on the tip. Both the radiation source and photodetector can be mounted at the tip. Both the radiation source and photodetector can be in the console (or otherwise not mounted at the tip).

Specifically, in an embodiment, the tip includes one opening and a photodetector (e.g., surface-mounted photodiode). In this specific embodiment, the one opening includes optical fiber which transmits radiation from a source diode to tissue. The source diode is located at the console. The photodetector, located at the tip, then receives the radiation from the tissue. The photodetector is connected to the console using electrical wires.

In another embodiment, the tip includes one opening and one or more radiation sources (e.g., LEDs). In this specific embodiment, the one or more LEDs mounted on the tip transmit radiation to the tissue. The one opening includes optical fiber which receives the radiation transmitted through the tissue. The optical fiber is connected to the console so that the received radiation from the tissue can be transmitted to photodetectors in the console.

In another embodiment, the tip does not include optical fibers, openings, or a resin. For example, in a specific embodiment the tip includes one or more radiation sources (e.g., LED chips) and one or more photodetectors (e.g. photodiode chip) mounted to the tip or mounted to a thin-film circuit board. There may be, for example, two LED chips each emitting different wavelengths of radiation (e.g., a first LED chip emitting red light and a second LED emitting infrared light). In a further embodiment, there is one LED chip that is capable of emitting multiple wavelengths of radiation (e.g., a multiwavelength radiation source).

One or more components can be mounted on a surface of the blade other than a tissue-facing surface, which will face or touch the tissue. The components can be mounted on a back surface of the blade, which is on the other side of the blade or opposite of the tissue-facing surface. There can be a channel in the blade (or a groove along an edge of the blade), which conducts light or radiation to and from the tissue-facing surface to the components mounted on back surface.

In various embodiments, some components can be mounted on the tissue-facing surface while others are mounted on the back surface. All components are mounted on the tissue-facing surface. All components are mounted on the back surface.

Similarly, when the components are mounted to a circuit board, this circuit board can be mounted on the tissue-facing surface or back surface of the blade. For example, the circuit board may be mounted to second surface portion 1129. In this specific embodiment, the tip may then include openings 1123a and 1123b so that light from the LEDs mounted to the circuit can be transmitted to the tissue. And so that light transmitted from the tissue can be received by photodiodes mounted to the circuit board.

Further, a thin-film circuit board can be attached to the tip (e.g., attached to first surface portion 1126). In this embodiment, the first surface portion and second surface portion do not have any openings. That is, the first and second surface portions are continuous and uninterrupted by any openings. The attachment of the thin-film circuit board may be by any means including, for example, soldering, welding, brazing, or by applying cements, adhesives, or glues.

The thin-film circuit board or other electric components (e.g., LEDs and photodiodes) mounted at the tip are connected to the console using electrical wires (e.g., flexible flat cable and ribbon cable). In a specific embodiment, the electrical wires run within a channel in the elevator. For example, at least a portion of the handle of the elevator is hollow so that the electrical wires can pass through.

As another example, the handle includes a groove into which the electrical wires are recessed. In another embodiment, the electrical wires run along the outside of the elevator. For example, the electrical wires can run along the outside of the handle instead of inside a channel in the handle. In this specific embodiment, the electrical wires may be secured to the handle using, for example, heat-shrink tubing.

In a specific embodiment, the source, detector structures, or both are positioned on the same plane as the first surface portion. In another embodiment, the source, detector structures, or both are positioned above the first surface portion. This may be done to help ensure that the source, detector structures, or both are positioned near the tissue to be measured. In yet another embodiment, the source, detector structures, or both are positioned below the first surface portion. This may be done to help ensure that the source, detector structures, or both are protected from contamination.

In a specific embodiment, first surface portion 1126 and third surface portion 1132 may be flat, as shown, or curved or angled (e.g., concave or convex) or have another contour (e.g., ogee, French curve, arch, or hook) as desired for the particular operation or intended use. Second surface portion 1129 and fourth surface portion 1135 may be rounded or convex as shown or may have another contour (e.g., flat) as desired for the particular operation or intended use. The various contours may be part of a tip that also has one or more contours in other dimensions or planes.

In a further embodiment, one or more surfaces may be textured. For example, the surface may include multiple nubs, bumps, ribs, or protrusions. These surface features may help to lift portions of the nerve away from the blade surface so as to minimize any crushing of blood vessels running alongside the nerve or to promote aeration of the nerve.

In yet another embodiment, one or more surfaces may have multiple holes to promote, for example, aeration of the nerve.

In a specific embodiment, a distal end 1142 has a rounded, curved, or convex edge 1138. The curved or convex edge may have the shape of a semicircle, oval, or ellipse—just to name a few examples. Such a shape may help to prevent injury to tissue. For example, during use, the user inserts the first blade portion between two pieces of tissue (e.g., nerve and other tissue) in order to measure a gap between the tissues. Certain tissue, such as a nerve, may be very fragile. The convex edge thus helps to prevent contact injury to the nerve and other tissues surrounding the nerve.

In other embodiments, the distal end may include a different shape or profile including, for example, points, straight edges, concave edges, rounded corners, and combinations of these. For example, FIG. 12 shows a tip 1250 with a distal end 1252 having a straight edge 1254 with rounded corners 1256.

It should also be appreciated that an embodiment of the tip may include curved or rounded edges in one or more planes. For example, FIG. 13 shows a partial longitudinal cross section of a tip 1360 with a distal end 1362 having a rounded side 1364. Tip 1360 also includes a first blade portion 1366 and a resin 1368.

In an embodiment, as shown in FIG. 13, the tip tapers or becomes gradually thinner towards the distal end. In a specific embodiment, both the first blade portion and resin taper towards the distal end. That is, the thickness of the first blade portion and resin become gradually thinner towards the distal end. For example, in FIG. 13, openings 1370*a* and 1370*b* include fiber optic cables 1372 and 1374, respectively. A length L1 of opening 1370*a* may be greater than a length L2 of opening 1370*b*. Opening 1370*b* is closer to the distal end of the first blade portion than opening 1370*a*. And, the thickness of the resin over the opening 1370*a* may be greater than the thickness over opening 1370*b*.

In another embodiment, the thickness of the first blade portion may remain constant and the resin may taper. For example, the length of opening 1370*a* may be the same as the length of opening 1370*b*. However, the thickness of the resin over the opening 1370*a* may be greater than the thickness over opening 1370*b*.

In still another embodiment, the thickness of the resin may remain constant and the thickness of the first blade portion may taper. For example, the length of opening 1370*a* may be greater than the length of opening 1370*b*. However, the thickness of the resin over opening 1370*a* may be the same as the thickness over opening 1370*b*.

The tapering of the tip helps to prevent damage to the nerve and other tissue during use of the elevator. For example, one use of the elevator is as a thickness gauge. That is, to measure the distance or thickness of a gap between a nerve and other tissue. As the tip is inserted between the nerve and other tissue, the tapering helps to ensure that any movement of the nerve away from the tissue is gradual.

However, in yet another embodiment, the tip does not taper. That is, the thickness of the blade and resin may remain constant.

FIG. 14 shows a right-hand side view of the first embodiment of tip 1105, including first blade portion 1110, second blade portion 1116, and openings 1123*a* and 1123*b*.

In a specific embodiment, the second blade portion and first blade portion are generally planar members. The second blade portion may lie on a plane 1415 while the first blade portion may lie on a different plane, i.e., a plane 1420. Planes 1415 and 1420 may intersect and form an angle A6.

In a specific embodiment, angle A6 in an obtuse angle. For example, angle A6 may be about 105 degrees, but may range from about 90 degrees to about 170 degrees, including 90, 95, 100, 101, 102, 103, 104, 105, 106, 107, 108, 109, 110, 115, 120, 130, 140, 150, 160, 170, more than 170 degrees, and less than 90 degrees depending upon the application.

In a specific embodiment, the openings (e.g., opening 1123*a* and 1123*b*) are positioned on the tip outside of an interior 1425 of angle A6. For example, the openings may be positioned on first surface portion 1126 as shown, third surface portion 1132, or both.

In another embodiment, the openings may be positioned within the interior of angle A6. For example, the openings may be positioned on second surface portion 1129, fourth surface portion 1135, or both.

FIG. 15 shows a left-hand side view of the first embodiment of tip 1105, including a resin 1510 between first surface portion 1126 and second surface portion 1129 and between third surface portion 1132 and fourth surface portion 1135.

Dimensions T9, T12, and T15 indicate the thickness of the blade, resin, and blade plus resin, respectively, at proximal end 1112.

In a specific embodiment T9 is about 0.5 millimeters, but may range from about 0.3 millimeters to about 4 millimeters. In some embodiments, T9 may be less than 0.3 millimeters or greater than 4 millimeters.

In a specific embodiment, T12 is about 0.5 millimeters, but may range from about 0.3 millimeters to about 4 millimeters. In some embodiments, T12 may be less than 0.3 millimeters or greater than 4 millimeters.

In a specific embodiment, T15 is about 1.5 millimeters, but may range from about 0.5 millimeters to about 4 millimeters. In some embodiments, T15 may be less than 0.5 millimeters or greater than 4 millimeters.

In an implementation, the fiber optic cables that run to the sensor openings on the first surface portion are encapsulated by an epoxy (i.e., adhesive or similar material or compound) which cures into resin 1510. Some examples of resins include thermosetting resins, polyester resins, amino resins, polyamide resins, polyvinyl butyral resins, acrylic resins, phenol formaldehyde resins, ketone formaldehyde resins, and alkyd resins.

In a specific embodiment, the resin is left exposed or uncovered. In other words, in an embodiment, surface 1129 is the surface of the resin which will be left exposed or uncovered.

In another embodiment, the surface of the resin may be at least partially covered with a covering. The covering may be used to, for example, enhance the aesthetic appearance of the elevator, make the surface more smooth than the original starting material so that the blade can easily slide between the tissues, increase the chemical resistance of the resin, or provide other desirable properties. As an example, the covering may be a nonmetal shell. Nonmetal shells such as plastics are generally not thermally conductive as it is generally undesirable to thermally heat the nerve. Other examples of coverings include paint, ceramic, silicon, one or more layers of epoxy, graphite, or any other biocompatible material.

The resin (or other material) holds the fibers in place, prevents damage to the fibers, and prevents detaching of the fibers from the sensor openings during use. The shape of the resin or other material may be sculpted as shown to facilitate ease in use of the device.

In a specific implementation, the number of fiber optic cables in the resin equals the number of openings on the first surface portion. For example, if there are two openings on the first surface portion, then there will be two fiber optic cables in the resin. If there are three openings, then there will be three fiber optic cables. If there are four openings, then there will be four fiber optic cables, and so forth.

In another embodiment, the number of fiber optic cables in the resin may not equal the number of openings on the first surface portion. The number of fiber optic cables may exceed the number of openings on the first surface portion. For example, the bottom surface may include one or more openings that each includes two, three, four, five, six, seven, or more than seven ends fiber optic cable. In yet another embodiment, the number of fiber optic cables in the resin may be less than the number of openings on the first surface portion. For example, one or more openings on the first surface portion may include electrical wire instead of fiber optic cable.

In a specific embodiment, the thickness of the tip is thinner at the distal end than at the proximal end. The thickness of the tip at distal end 1142 may be about 0.5 millimeters, but may range from about 0.2 millimeters to about 5 millimeters. This includes, for example, 0.3, 0.4, 0.5, 0.6, 0.7, 0.8, 0.9, 1, 1.5, 2, 2.5, 3, 3.5, 4, 4.5, 5, or more than 5 millimeters. In other embodiments the thickness may be less than 0.3 millimeters. Some applications may use a thicker tip when, for example, a larger gap is desired between the nerve and other tissue. Other applications may use a thinner tip when, for example, a smaller gap is desired between the nerve and other tissue.

As was explained in the discussion accompanying FIG. 13, the thickness of the tip may depend on the thickness of the resin, blade, or both. Typically, the thickness of the resin at the proximal end of the first blade portion (i.e., T12) will be thicker than the thickness of the resin at the distal end of the first blade portion. In an embodiment, the thickness of the resin may become progressively thinner as the first blade portion extends from the proximal end to the distal end. The thickness of the resin may be proportional to the thickness or diameter of fiber optic cables that may be sealed in the resin and the desired gap between a nerve and other tissue. Generally, thicker or larger diameter fiber optic cables will result in a thicker resin. Likewise, a larger desired gap between a nerve and other tissue will result in a thicker resin.

In a specific implementation, thickness T9 of the first blade portion remains constant from the proximal end to the distal end. This helps to provide strength so that the blade does not improperly flex or break during use. However, in other implementations, the thickness may not be constant. For example, the thickness of the first blade portion may become progressively thinner or taper as one moves from the proximal end towards the distal end.

FIG. 16 shows a top view of tip 1105 including first blade portion 1110 coupled to second blade portion 1116. Dimensions L15 and L17 indicate the lengths of the first and second blade portions, respectively. A dimension L19 indicates the length of the tip (i.e., length of first blade portion plus length of second blade portion). A dimension W12 indicates a width of the tip at a proximal end 1650. A dimension W14 indicates a width of the tip at a distal end 1655.

In an embodiment, length L15 of the first blade portion is greater than length L17 of the second blade portion. For example, length L15 may be about 1.5 times greater than L17, but may range from about 1.2 to about 3 times greater than length L17.

In an embodiment, width W14 is greater than width W12. For example, width W14 may be about ten percent greater than width W12, but may range from about eight percent to about fifteen percent greater. In another embodiment width W14 and W12 may be the same. For example, a side edge 1660 may be parallel to a side edge 1665. In still another embodiment, width W12 may be greater than width W14.

Table B below shows several dimensions for the tip. However, it should be appreciated that these dimensions may vary depending upon the application.

TABLE B

| Dimension | First Implementation (millimeters) | Second Implementation (millimeters) | Third Implementation (millimeters) | Range of Dimensions (millimeters) |
|---|---|---|---|---|
| Tip length (L19) | 15 | 10 | 19 | 9-21 |
| First blade portion length (L15) | 10 | 7 | 13 | 6-14 |
| Second blade portion length (L17) | 5 | 3 | 6 | 3-7 |
| Tip width at proximal end (W12) | 3 | 2.1 | 4 | 1.9-5 |
| Tip width at distal end (W14) | 4 | 2.8 | 5 | 2.5-6 |

FIG. 17 shows a cross section view of tip 1105 including first blade portion 1110, resin 1310, and a fiber optic cable 1705 connected to opening 1123a.

In a specific embodiment, an opening for a source or detector structure, such as opening 1123a (or 1123b) passes from a first side 1710 of the first blade portion towards a second side 1715 of the first blade portion. The opening may pass through the second side as shown in the example in FIG. 17.

In another embodiment, the opening may not pass through the second side. For example, the fiber optic cable, instead of being sealed in the resin may be at least partially sealed within the first blade portion. That is, the first blade portion may include a channel through which the fiber optic cable runs. The channel may then be connected to the opening which may be exposed on the first side. In this specific implementation, resin 1310 may not cover an entire surface of the blade.

In an embodiment, the resin covers the openings on the second side. This helps to ensure that the fiber optic cable is secured in the opening. The resin may further completely cover the second side or at least partially cover the second side.

The cross section of the resin may be rounded, contoured, or curved. For example, the thickness of the resin below the opening may be thicker than the thickness of the resin at side edges 1720 and 1722. The thickness of the resin may taper or become progressively thinner moving outwards from the opening.

The contours or curves help to insure that the nerve or other tissue is not damaged while the elevator is being used. However, in other implementations, the cross section of the resin may not be contoured. For example, the cross section may be polygonal (e.g., square, rectangle, and trapezoid).

Figure 18:
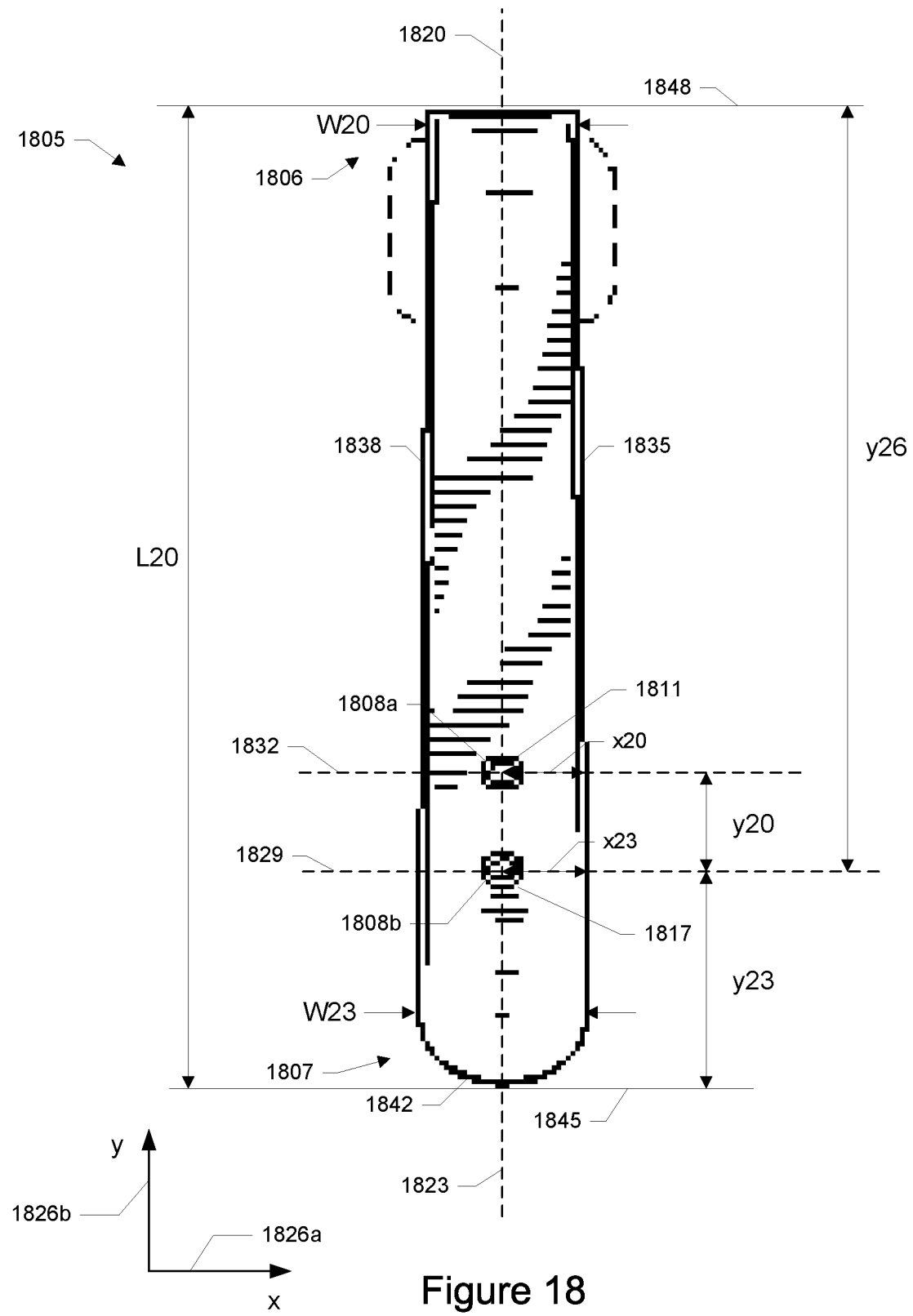
FIG. 18 shows a front view of a first blade portion of the tip with a single light source and single detector symmetrical array.

FIG. 18 shows a view of a first blade portion or probe 1805 in a first geometric arrangement with two openings. This geometric arrangement includes a single light source and single detector in a symmetrical array. The first blade portion has a width W20 at a proximal end 1806, a width W23 at a distal end 1807, and a length L20 from the proximal end to the distal end. A first opening 1808a includes a source structure 1811. A second opening 1808b includes a detector structure 1817.

In a specific implementation, width W20 and width W23 are different. For example, width W23 may be greater than width W20. The width of the first blade portion may become progressively greater as one moves from the proximal end towards the distal end. In a specific implementation, width W23 is about 12 percent greater than width W20, but width W23 may range from about 7 percent to about 15 percent greater than width W20. This includes, for example, 7, 8, 9, 10, 11, 12, 13, 14, 15, more than 15, and less than 7 percent greater. Width W20, W23, or both may be less than or equal to a diameter of the first opening plus a diameter of the second opening. In a further embodiment, width W20, W23, or both may be less than three times a diameter of the first opening. In a further embodiment, width W20, W23, or both may be less than four times a diameter of the first opening.

The thinner proximal end of the first blade portion as compared to the wider distal end of the blade provides several benefits. For example, the thinner proximal end allows the user to see the surrounding tissue without the blade obstructing the user's view. The wider distal end helps to ensure the length of the gap between the nerve and other tissue.

Typically, the length of the first blade portion is greater than either width W23 or width W20. In a specific implementation, L20 is about six times greater than width W23 or width W20, but may range from about three to about seven times greater. This includes, for example, three, four, five, six, seven, or more than seven times greater than width W23 or width W20. In another implementation, L20 may be less than three times greater than width W23 or width W20. The length of the first blade portion helps to ensure that the blade can properly reach into the surgical site so that the gap between the nerve and other tissue can be determined.

Typically, the surface area of the first surface portion will be greater than the surface area of the openings. For example, the surface area of the first surface portion may be about two-hundred and fifty to about three-hundred and fifty times greater than the combined surface area of the openings. In other implementations, the surface area of the first surface portion will be less than or equal to the surface area of the openings.

The source and detector structures generally include optical fiber that are used to measure oxygen saturation levels in tissue, such as a nerve. For example, the source structure may include an end of a first optical fiber where the opposite end is connected to a light source. The detector structure may include an end of a second optical fiber where the opposite end is connected to a photodetector.

In an implementation, optical fiber is used having a diameter of about 0.5 millimeters, but may range from about 0.2 millimeters to about 5 millimeters. For example, the diameter may be about 0.75, 1, 1.5, 2, 2.5, 3, 3.5, 4, 4.5, or 5 millimeters, or larger. In other implementations, smaller diameter fibers (i.e., less than 0.5 millimeters) may be used.

Generally, the diameter of the fiber optic cable and corresponding opening will be about the same. Smaller openings allow, for example, smaller tips and thus smaller incisions. Larger openings, allow, for example, more light to be transmitted into the tissue, and received from the tissue.

In a specific implementation, the source and detector structures are in a symmetrical arrangement. For example, each source and detector structure has a reference point. The reference point may be the centers of the sources and detectors if, for example, the sources and detectors have circular shapes. Alternatively, the reference point may be defined as some other point, so long as the definition is consistent among the sources and detectors.

Lines 1820 and 1823 pass through the source and detector structures. Line 1820 is parallel to a y-axis 1826*b* and passes through the reference point of source structure 1811. Line 1823 is parallel to the y-axis and passes through the reference point of detector structure 1817. Lines 1820 and 1823 are coincident. That is, source structure 1811 is in a symmetrical arrangement with respect to detector structure 1817.

A line 1829 is parallel to an x-axis 1826*a* and passes through the reference point of the detector structure. A line 1832 is parallel to the x-axis and passes through the reference point of the source structure. Source structure 1811 and detector structure 1817 are separated by a distance y20 between lines 1829 and 1832.

The separation between the source and detector structures may vary widely. Generally, the separation between the source and detector structures is proportional to the depth in a tissue at which a tissue oxygen saturation measurement or other measurement is desired.

By way of example, distance y20 is about 1.5 millimeters, but may range from about 1 millimeter to about 5 millimeters. For example, distance y20 may be about 1.5, 2, 2.5, 3, 3.5, 4, 4.5, 5, or more than 5 millimeters. In other implementations, distance y20 may be less than 1.5 millimeters.

A distance x20 is between line 1820 and an edge 1835. That is, the source structure may be offset by distance x20 from edge 1835. Edge 1835 marks a side edge (e.g., right-hand side edge) of the first blade portion. An edge 1838 marks another side edge (e.g., left-hand side edge) that is opposite edge 1835. The source structure is typically placed equidistant between edge 1835 and an edge 1838. For example, if the distance between edges 1835 and 1838 is S then x20 will be S/2. However, as discussed in this application, in various implementations a source structure may not be equidistant between edges 1835 and 1838.

In an embodiment, distance x20 is at least about 0.5 millimeters. However, distance x20 may vary from about 0.5 millimeters to about 6 millimeters depending on the application.

A distance x23 is between line 1820 and edge 1835. That is, the detector structure may be offset by distance x23 from edge 1835. The detector structure is typically placed equidistant between edge 1835 and an edge 1838. For example, if the distance between edges 1835 and 1838 is D then x20 will be D/2. However, as discussed in this application, in various implementations a detector structure may not be equidistant between edges 1835 and 1838.

In an embodiment, distance x23 is at least about 0.5 millimeters. However, distance x23 may vary from about 0.5 millimeters to about 6 millimeters depending on the application.

Typically, the source structure, detector structure, or both are located closer to an edge 1842 at the distal end of the first blade portion than the proximal end of the first blade portion. That is, a first distance from opening 1808*a* to the proximal end will be greater than a second distance from opening 1808*a* to the distal end. Likewise, a third distance from opening 1808*b* to the proximal end will be greater than a fourth distance from opening 1808*b* to the distal end.

For example, a line 1845 that is parallel to the x-axis passes through or is tangent to edge 1842. A line 1848 that is parallel to the x-axis passes through the proximal end of the first blade portion.

A distance y23 is between lines 1845 and 1829. A distance y26 is between lines 1829 and 1848. Generally, distance y26 will be greater than distance y23. In a specific implementation, distance y26 is about 4.8 times greater than distance y23. However, distance y26 may range from about 3 to about 6 times greater than distance y23. For example, distance y26 may be 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, or more than 5.5 times greater than distance y23. In other implementations, distance y26 may be less than 3 times greater than distance y23.

The variations of the relationship between distance y23 and distance y26 reflects the varying dimensions of a nerve, other tissue, or cavity into which the elevator will be inserted. For example, the diameter of a nerve may vary from patient-to-patient. It may also vary along the length of a nerve. The diameter of a nerve may range from about 1 millimeter to about 5 millimeters. For example, the nerve root in the lower back of a typical adult is about 4 millimeters in diameter. Because edge 1842 is the leading edge to be inserted in the gap between a nerve and other tissue, locating the source and detector structures near edge 1842 allows light to be transmitted from the source structure into the nerve and then received by the detector structure.

Generally, distance y23 will be proportional to the size of the nerve, the desired gap (i.e., desired distance between the nerve and other tissue), or both. That is, smaller nerves will result in a smaller distance y23 while larger nerves will result in a greater distance y23. For example, where the nerve is small, such as the nerve of a child, the source and detector structures may be located closer to edge 1842 so that the source and detector structures will be located next to the nerve. Thus, light can be transmitted into the nerve and received from the nerve. Where, however, the nerve is large, such as the nerve of an adult, the source and detector structures may be located further away from edge 1842.

Likewise, distance y23 may also be proportional to the desired gap between the nerve and other tissue. That is, smaller desired gaps will result in a smaller distance y23 while larger desired gaps will result in a greater distance y23. This is because in a specific implementation, the thickness of the first blade portion as seen in FIG. 13 becomes progressively greater as one moves from the distal end of the first blade portion towards the proximal end of the first blade portion. Thus, a small desired gap will result in a smaller y23 as the source and detector structures will be located closer to the thinner portion of the first blade portion. Conversely, a large desired gap will result in a greater y23 as the source and detector structures will be located closer to the thicker portion of the first blade portion.

Although the example shown in FIG. 18 shows detector structure 1817 closer to edge 1842 than source structure 1811, it should be appreciated that in other implementations source structure 1811 may be positioned closer to edge 1842 than detector structure 1817.

Typically, the source and detector structures are located along one or more axes that are parallel to the longitudinal axis of the first blade portion. However, in other implementations, the source and detector structures may be located along other axes.

In another implementation, the arrangement of sources and detectors is asymmetrical. An asymmetrical arrangement of sources and detectors is discussed in U.S. Pat. No. 7,355,688, which is incorporated by reference. Any of the asymmetrical arrangements of sources and detectors discussed in that patent is applicable to the sources and detectors in this application.

Figure 19:
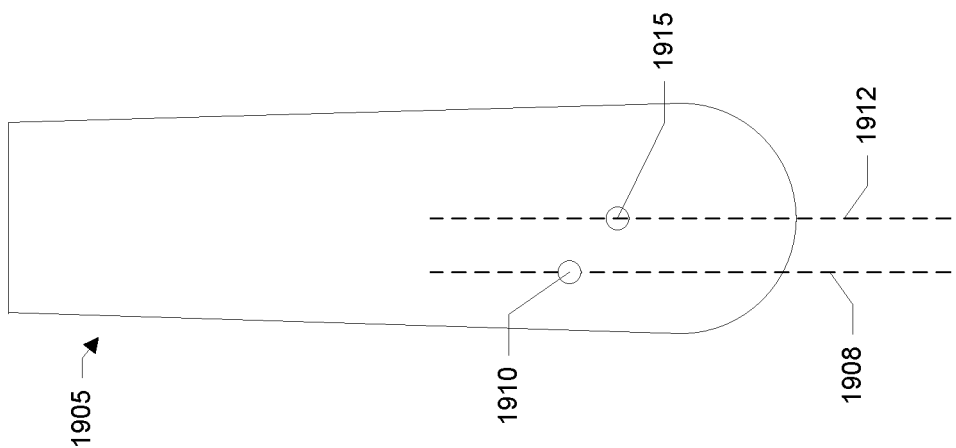
FIG. 19 shows a front view of a first blade portion with a single light source and single detector asymmetrical array.

FIG. 19 shows a view of a probe 1905 in a second geometric arrangement with two openings. This geometric arrangement includes a single light source and single detector in an asymmetrical array. A first axis 1908 passes through the reference point of a source structure 1910. A second axis 1912 passes through the reference point of the detector structure 1915. The first axis is parallel to the second axis, but offset to the left side of the second axis, i.e., the first and second axes are not coincident.

In another embodiment, a first axis passes instead through the reference point of the detector structure and the second axis passes through the reference point of the source structure. The first axis is parallel to the second axis, but offset to the left side of the second axis, i.e., the first and second axes are not coincident.

Figure 20:
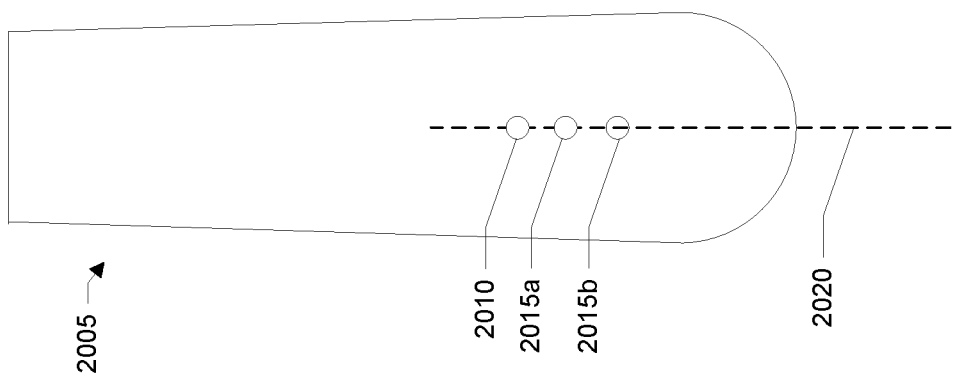
FIG. 20 shows a front view of a first blade portion with a single light source and two detector asymmetrical array.

FIG. 20 shows a view of a probe 2005 in a first geometric arrangement with three openings in a symmetrical arrangement. This arrangement includes a single light source and two detectors in a symmetrical array. A first distance is between a source structure 2010 and a first detector structure (2015a). A second distance is between the first detector structure and a second detector structure (2015b). The source and detector structures may be arranged on a line 2020. In this first geometric arrangement of three openings, the first and second distances are equal.

However, many other different geometric arrangements are possible. For example, in a second geometric arrangement, the first distance is less than the second distance.

In a third geometric arrangement, the first distance is greater than the second distance.

FIG. 20 shows various geometric arrangements of source and detector structures relative to a single axis where the source and detector structures are arranged on the same line (i.e., line 2020). However, other geometric arrangements may instead or additionally have distances between source and detector arrangements relative to a second axis.

Figure 21:
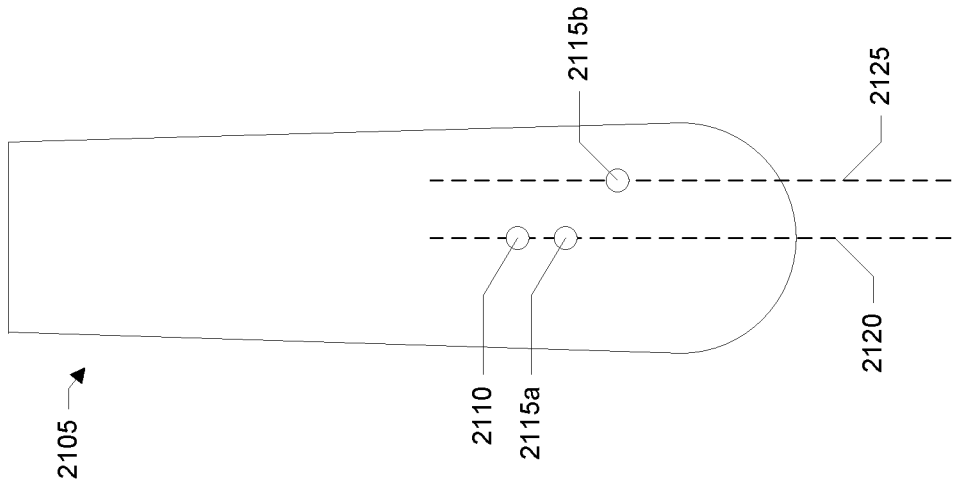
FIG. 21 shows a front view of a first blade portion with a single light source and two detector asymmetrical array.

For example, FIG. 21 shows a view of a probe 2105 in a fourth geometric arrangement. This geometric arrangement includes a single light source and two detectors in an asymmetrical arrangement. This specific example shows an asymmetry relative to an x-axis.

A first distance is between a source structure 2110 and a first detector structure 2115a. A second distance is between the first detector structure and a second detector structure 2115b. In the example shown in FIG. 21, the first distance is less than the second distance.

A first axis 2120 passes through the reference point of source structure and first detector structure. A second axis 2125 passes through the reference point of the second detector structure. The first axis is parallel to the second axis, but offset to the left side of the second axis, i.e., the first and second axes are not coincident.

However, many other different geometric arrangements are possible. For example, in a fifth geometric arrangement, a first axis passes through the reference point of the first and second detector structures. A second axis passes through the reference point of the source structure. The first axis is parallel to the second axis, but offset to the left side of the second axis, i.e., the first and second axes are not coincident. In this second geometric arrangement, the first distance is greater than the second distance.

In a sixth geometric arrangement, a first axis passes through the reference point of the first source structure and second detector structure. A second axis passes through the reference point of the first detector structure. The first axis is parallel to the second axis, but offset to the left side of the second axis, i.e., the first and second axes are not coincident. In this third geometric arrangement, the first distance is equal to the second distance.

In a seventh geometric arrangement, a first axis passes through the reference point of the first detector structure. A second axis passes through the reference point of the first source structure and second detector structure. The first axis is parallel to the second axis, but offset to the left side of the second axis, i.e., the first and second axes are not coincident. In this fourth geometric arrangement, the first distance is equal to the second distance.

FIG. 22 shows a view of a probe 2205 in an eighth geometric arrangement with three openings. The probe includes one light source and two detectors in an asymmetrical array. In the implementation shown in FIG. 22, the three openings arranged on a line. A first opening includes a source structure 2215. Second and third openings include detector structures 2220a and 2220b, respectively.

A line 2225 which is parallel to a y-axis 2230b passes through the reference point for each of the source and detector structures. A line 2235 which is parallel to an x-axis 2230a passes through the reference point of source structure 2215. A line 2240 which is parallel to the x-axis passes through the reference point of detector structure 2220a. A line 2245 which is parallel to the x-axis passes through the reference point of detector structure 2220b.

The asymmetrical source and detector array of FIG. 22 includes source structure 2215 and detector structure 2220b, with detector structure 2220a interposed between source structure 2215 and detector structure 2220b. Source structure 2215 and detector structure 2220b are located at opposite ends of the array, while detector structure 2220a is located in a middle, but off-center portion of the array.

For example, a distance y30 is between lines 2235 and 2240. A distance y33 is between lines 2240 and 2245. Distance y30 is different from distance y33. Although distance y30 is shown as being greater than distance y33, it should be appreciated that distance y33 may instead be greater than distance y30. The difference between distance y30 and distance y33 is generally characteristic of the offset arrangement, or substantially unbalanced arrangement of the source structure relative to the detector structures.

A distance y36 is between lines 2235 and 2245. In a specific implementation, distance y33 is about one-third of the distance y36 and distance y30 is about two-thirds of the distance y36. For example, if y36 is 5 millimeters then y33 is 5/3 millimeters and y30 is 10/3 millimeters (i.e., 2/3*5 millimeters is 10/3 millimeters).

However, other implementations may include a symmetrical source-detector arrangement. For example, distance y30 may be the same as distance y33 as shown in FIG. 20.

FIG. 23 shows view of a probe 2305 in a first geometric arrangement with four openings. This arrangement includes two light sources and two detectors in a symmetrical array. The four openings arranged on a line. First and second openings include source structures 2310a and 2310b, respectively. Third and fourth openings include detector structures 2315a and 2315b, respectively.

A line 2320 which is parallel to a y-axis 2325b passes through the reference point for each of the source and detector structures. A line 2330 which is parallel to an x-axis 2325a passes through the reference point of source structure 2310a. A line 2335 which is parallel to x-axis 2325a passes through the reference point of source structure 2310b. A line 2340 which is parallel to the x-axis passes through the reference point of detector structure 2315a. A line 2345 which is parallel to the x-axis passes through the reference point of detector structure 2315b.

The two light source and two detector array of FIG. 23 includes source structure 2310a and detector structure 2315b positioned at opposite ends of the array, while source structure 2310b and detector structure 2315a are interposed between source structure 2310a and detector structure 2315b. That is, the arrangement shown in FIG. 23 provides the furthest separation between a source and detector structure (i.e., 2310a and 2315b) by positioning them on opposite ends of the array.

Separating source structure 2310a and detector structure 2315b on opposite ends of the array has advantages over other arrangements that may position the source structures on opposite ends of the array with the detector structures interposed between. One advantage is that the light emitted from source structure 2310a can travel deeper into the tissue before it is received by detector structure 2315b. Another advantage is that the first blade portion may be constructed with a very small size and therefore can be used in clinical applications where smaller instruments are advantageous because only a small incision is required to use them. Applications include, for example, spinal nerve root oxygenation measurement and monitoring in digit replantation.

In a specific implementation, the two-light-source and two-detector array is symmetrical. That is, the spacing between adjacent sources and detectors is equal. For example, a distance y40 is between lines 2330 and 2335. A distance y43 is between lines 2335 and 2340. A distance y46 is between lines 2340 and 2345. A distance y49 is between lines 2330 and 2345.

In a specific implementation, distances y40, y43, and y46 are the same. In a specific implementation, distances y40, y43, and y46 are each one-third the distance y49. For example, if y49 is 5 millimeters then y40, y43, and y46 are all 5/3 millimeters.

FIG. 24 shows a probe 2405 in a second geometric arrangement with four openings in an asymmetrical arrangement. In an embodiment, at least one of the openings is not aligned or is asymmetrical with the other openings. In another implementation, there are two openings that are not aligned with the other openings. In yet another implementation, there are at least three openings that are not aligned to each other. In still another implementation, there are at least four openings that are not aligned to each other.

A specific implementation of the figure has two light sources and two detectors in an asymmetrical array. As shown in the example of FIG. 24, three openings arranged on the same line and a fourth opening arranged offset from the line. First and second openings include source structures 2410a and 2410b, respectively. Third and fourth openings include detector structures 2415a and 2415b, respectively.

A line 2420 which is parallel to a y-axis 2425b passes through the reference point for source structures 2410a and 2410b and detector structure 2415a. A line 2430 which is parallel to y-axis 2425b passes through the reference point for detector structure 2415b.

A line 2435 which is parallel to an x-axis 2425a passes through the reference point of source structure 2410a. A line 2440 which is parallel to x-axis 2425a passes through the reference point of source structure 2410b. A line 2445 which is parallel to the x-axis passes through the reference point of detector structure 2415a. A line 2450 which is parallel to the x-axis passes through the reference point of detector structure 2415b.

A distance y50 is between lines 2435 and 2450. A distance y53 is between lines 2435 and 2440. A distance y56 is between lines 2440 and 2445. A distance y59 is between lines 2445 and 2450.

Lines 2420 and 2430 although parallel to the y-axis are not coincident. That is line 2420 is offset from line 2430 by a distance x30 along the x-axis, i.e., there is a lack of symmetry with respect to the x-axis. In a specific implementation x30 is about 0.5 millimeters. However, x30 may range from about 0.1 millimeters to about 2.5 millimeters. For example, x30 may be 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5 or more than 2.5 millimeters. In other implementations, x10 may be less than 0.1 millimeters.

As a further example, in an asymmetrical arrangement, the sources and detectors are arranged so there is a first distance between a first source structure (e.g., 2410a) and a first detector structure (e.g., 2415a) and a second distance between the second source structure (e.g., 2410b) and a second detector structure (e.g., 2415b), where the first and second distances are not equal.

For example, in a specific implementation, the distance along the y-axis between adjacent sensors is $$\frac{n}{(m-1)},$$

where n is the distance along the y-axis between the furthest source and detector pair and m is the number of sensors. Thus, in a specific implementation including four sensors and a y-axis distance of 5 millimeters between the furthest source and detector pair, the y-axis distance between adjacent sensors is 5/3 millimeters $$\left(\text{i.e., } \frac{5 \text{ millimeters}}{(4-1)} = \frac{5}{3} \text{ millimeters}\right).$$

In this example then, the first distance (i.e., source structure 2410a to detector structure 2415a) is 10/3 millimeters (i.e., 3.3 millimeters). The second distance (i.e., source structure 2410b to detector structure 2415b) is 3.4 millimeters, where x30 is 0.5 millimeters (i.e., second distance= $\sqrt{(0.5)^2+(3.3)^2}=3.4$).

In a specific implementation, an attenuation ratio is used to determine tissue oxygenation (StO$_2$), hemoglobin concentration (Hgb), or both. The attenuation ratio is the ratio of light attenuation emitted by a source and received by a detector at a wavelength to that of another wavelength. The attenuation ratio can then be generally expressed in the following equation:

$$R(S, D) = \frac{U^{\lambda_1}(S, D)}{U^{\lambda_2}(S, D)} \quad (1)$$

where $U^{\lambda_i}(S,D)$ for i=1, 2, is the light intensity received by the detector when the source is on at wavelength $\lambda_i$.

In a specific implementation, light is emitted from the source structures at two different wavelengths including, for example, 690 nanometers and 830 nanometers. For the source-detector array shown in FIG. 24, there are four source-detector pairs including: $(S_1, D_1)$, $(S_1, D_2)$, $(S_2, D_1)$, and $(S_2, D_2)$. $S_1$ and $S_2$ correspond to source structures

2410$a$ and 2410$b$, respectively. $D_1$ and $D_2$ correspond to detector structures 2415$a$ and 2415$b$, respectively.

For each source-detector pair $(S_i, D_j)$ for i=1, 2, there are two optical measurements including: $U^{690}(S_i, D_j)$ and $U^{830}(S_i, D_j)$. The attenuation ratio is thus defined as:

$$R(S_i, D_j) = \frac{U^{690}(S_i, D_j)}{U^{830}(S_i, D_j)} \tag{2}$$

In the automatic error-cancellation or self-calibration scheme, the system factors such as source intensity, detector gain, and loss of light in the optical fibers and connectors are cancelled automatically. The automatic error-cancellation scheme is discussed in more detail as equations 5a and 5b in U.S. Pat. No. 6,597,931, which is incorporated by reference.

For the linear sensor array, such as that shown in FIG. 24, one can form the following four quantities independent of these system factors:

$$\begin{cases} U^{(4)}(690, 690) = \dfrac{U(S_1^{690}, D_1)U(S_2^{690}, D_2)}{U(S_1^{690}, D_2)U(S_2^{690}, D_1)}, \\ U^{(4)}(690, 830) = \dfrac{U(S_1^{690}, D_1)U(S_2^{830}, D_2)}{U(S_1^{690}, D_2)U(S_2^{830}, D_1)}, \\ U^{(4)}(830, 690) = \dfrac{U(S_1^{830}, D_1)U(S_2^{690}, D_2)}{U(S_1^{830}, D_2)U(S_2^{690}, D_1)}, \\ U^{(4)}(830, 830) = \dfrac{U(S_1^{830}, D_1)U(S_2^{830}, D_2)}{U(S_1^{830}, D_2)U(S_2^{830}, D_1)} \end{cases} \tag{3}$$

For the attenuation ratio method, one takes the ratios of these four quantities:

$$\begin{cases} R_1 = \dfrac{U^{(4)}(690, 690)}{U^{(4)}(690, 830)} = \dfrac{R(S_2, D_2)}{R(S_2, D_1)}, \\ R_2 = \dfrac{U^{(4)}(690, 690)}{U^{(4)}(830, 690)} = \dfrac{R(S_1, D_1)}{R(S_1, D_2)}, \\ R_3 = \dfrac{U^{(4)}(690, 690)}{U^{(4)}(830, 830)} = \dfrac{R(S_1, D_1)R(S_2, D_2)}{R(S_1, D_2)R(S_2, D_1)} = R_1 R_2, \\ R_4 = \dfrac{U^{(4)}(690, 830)}{U^{(4)}(830, 690)} = \dfrac{R(S_1, D_1)R(S_2, D_1)}{R(S_1, D_2)R(S_2, D_2)} = \dfrac{R_1}{R_2}, \\ R_5 = \dfrac{U^{(4)}(690, 830)}{U^{(4)}(830, 830)} = \dfrac{R(S_1, D_1)}{R(S_1, D_2)} = R_2, \\ R_6 = \dfrac{U^{(4)}(830, 690)}{U^{(4)}(830, 830)} = \dfrac{R(S_2, D_2)}{R(S_2, D_1)} = R_1 \end{cases} \tag{4}$$

Note that $R_1$ depends only on $S_1$, $R_2$ depends only on $S_2$, and $R_4$ depends on both $S_1$ and $S_2$. Also note that $R_3$ can serve as a measure of signal quality, and $R_5$ and $R_6$ are not independent.

The following equation may be used without the self-calibration scheme. The attenuation ratio may be related to $StO_2$. $StO_2$ may be proportional to the attenuation ratio. Assuming a linear relation we have the equation:

$$StO_2(S_i, D_j) = kR(S_i, D_j) + b \tag{5}$$

where $R(S_i, D_j)$ is defined in equation (2), and k and b may be constants. We empirically take k=30 and b=0. If further $StO_2$ calibration is required for each individual sensor then the calibration data may be stored in a chip embedded in the sensor. Theoretically, the pair $(S_1, D_2)$ should be most sensitive to $StO_2$ change. The calibration factors (k, b) in equation (5) are console- and probe-dependent because the self-calibration scheme is not used in the $StO_2$ calculation and therefore system factors have not been cancelled. This complexity may be avoided by recording the ratio $$\frac{U^{690}(S_i, D_j)}{U^{830}(S_i, D_j)}$$

when a console-probe combination is used for the first time.

Furthermore, to avoid this problem, one may use the attenuation ratio method under the self-calibration scheme as described below.

With self-calibration, the self-calibrated attenuation ratio may be better than that without self-calibration for estimating the oxygenation. We assume:

$$StO_2(m) = k'R_m + b', m=1,2,4 \tag{6}$$

m=4 if both $S_1$ and $S_2$ are involved. m=1 if only $S_1$ is involved. m=2 if only $S_2$ is involved. The calibration factors (k', b') in equation (6) are now independent with respect to the console and probe. We empirically take k=100 and b=−30%.

Under a Monte Carlo simulation, when a light source is on, the light received by a detector is related to the source-detector separation by $$U(\rho) \approx \frac{e^{-\rho\sqrt{6\mu_{\mathit{eff}}}}}{\rho^2},$$

where $\mu_{\mathit{eff}}$ is the attenuation coefficient of the medium. A Monte Carlo simulation technique is discussed in *Approximate Theory of Photon Migration in a Two-layer Medium*, by H. Taitelbaum, S. Havlin, and G. H. Weiss, Applied Optics, 28(12), page 2245 (1989), which is incorporated by reference.

In the auto-calibration or error-cancellation scheme, $$U^{(4)} \approx G'_1 e^{-G'_2 \sqrt{6\mu_{\mathit{eff}}}},$$

where $G'_1$ and $G'_2$ are probe-geometry dependent. Assuming $\mu'_x$ is independent of wavelength, we have $$U^{(4)} \approx G'_1 e^{-G''_2 \sqrt{\mu_a}}.$$

The absorption coefficient is then calculated according to the following equation:

$$\mu_a = (G_1 + G_2 \ln U^{(4)})^2 \tag{7}$$

In the current algorithm, we take $G_1=0.5$ and $G_2=1$. Using the $\mu_a$ at the two wavelengths, Hgb is calculated in terms of $\mu_a$ at the two wavelengths.

The quantity $R_3$ in equation (4) can serve as a measure of signal quality, i.e., we define the signal quality factor by:

$$Q = R_3 = \frac{U(S_1^{690}, D_1)U(S_2^{690}, D_2)}{U(S_1^{690}, D_2)U(S_2^{690}, D_1)} \bigg/ \frac{U(S_1^{830}, D_1)U(S_2^{830}, D_2)}{U(S_1^{830}, D_2)U(S_2^{830}, D_1)} = \frac{U_1 U_6 U_{10} U_{13}}{U_2 U_5 U_9 U_{14}} \quad (8)$$

Additional detail on signal quality factors is discussed in U.S. patent application Ser. No. 11/162,380, filed Sep. 8, 2005, which is incorporated by reference.

It should also be appreciated that these equations may be applied to symmetrical source and detector arrangements such as that arrangement shown in the example of FIG. 18. The self-calibration scheme may include equations discussed in U.S. Pat. Nos. 6,516,209, 6,735,458, and 6,078, 833, and *New Optical Probe Designs for Absolute (Self-Calibrating) NIR Tissue Hemoglobin Measurements*, Proc. SPIE 3597, pages 618-631 (1999), which are incorporated by reference. The attenuation ratio method may also include techniques discussed in U.S. Pat. No. 6,587,701, which is incorporated by reference.

When the probe has two source openings and two detector openings, in a specific implementation, $StO_2$ is calculated using equation (6). That is, the self-calibration or auto-calculation scheme is used.

When the probe has one source opening and one detector opening, in a specific implementation, $StO_2$ is calculated using equation (5). That is, without using the self-calibration or auto-calculation scheme. The weighted average over source-detector pairs is not necessary because there is only one source-detector pair.

When the probe has one source opening and two detector openings, in a specific implementation, $StO_2$ is calculated using equation (5). The weighted average is over the two source-detector pairs.

FIG. 25 shows a probe 2505 in a third geometric arrangement with four openings in an asymmetrical arrangement. This specific example includes two source structures (2510a and 2510b) and two detector structures (2515a and 2515b). A first distance is between a first source structure (i.e., 2510a) and a second source structure (i.e., 2510b). A second distance is between the second source structure and a first detector structure (i.e., 2515b). A third distance is between the first detector structure and a second detector structure (i.e., 2515b).

A first axis 2520 passes through the reference point of the first and second source structures and second detector structure. A second axis 2525 passes through the reference point of the first detector structure. The first axis is parallel to the second axis, but offset to the left of the second axis, i.e., the first and second axes are not coincident. In this first geometric arrangement, the third distance is equal to the second distance. The first distance is less than the third or second distance.

However, many other different geometric arrangements are possible. For example, in a fourth geometric arrangement, a first axis passes through the reference point of the first and second source structures and first detector structure. A second axis passes through the reference point of the second detector structure. The first axis is parallel to the second axis, but offset to the left side of the second axis, i.e., the first and second axes are not coincident. In this fourth geometric arrangement, the first and second distances are equal. The third distance is greater than the first or second distances.

In a fifth geometric arrangement, a first axis passes through the reference point of the second source structure and first and second detector structures. A second axis passes through the reference point of the first source structure. The first axis is parallel to the second axis, but offset to the left side of the second axis, i.e., the first and second axes are not coincident. In this third geometric arrangement, the first distance is greater than the second distance, third distance, or both. The second distance is equal to the third distance.

In a sixth geometric arrangement, a first axis passes through the reference point of the first and second detector structures and the first source structure. A second axis passes through the reference point of the second source structure. The first axis is parallel to the second axis, but offset to the left side of the second axis, i.e., the first and second axes are not coincident. In this fourth geometric arrangement, the third distance is less than the first distance, second distance, or both. The first distance is equal to the second distance.

In a seventh geometric arrangement, a first axis passes through the reference point of the first and second source structures. A second axis passes through the reference point of the first and second detector structures. The first axis is parallel to the second axis, but offset to the left side of the second axis, i.e., the first and second axes are not coincident. In this fifth geometric arrangement, the second distance is greater than the first distance, the third distance, or both. The first distance equals the third distance.

In an eighth geometric arrangement, a first axis passes through the reference point of the first and second detector structures. A second axis passes through the reference point of the first and second source structures. The first axis is parallel to the second axis, but offset to the left side of the second axis, i.e., the first and second axes are not coincident. In this sixth geometric arrangement, the second distance is greater than the first distance, the third distance, or both. The first distance equals the third distance.

In a ninth geometric arrangement, a first axis passes through the reference point of the second source structure and second detector structure. A second axis passes through the reference point of the first source structure and first detector structure. The first axis is parallel to the second axis, but offset to the left side of the second axis, i.e., the first and second axes are not coincident. In this seventh geometric arrangement, the first, second, and third distances are equal.

In a tenth geometric arrangement, a first axis passes through the reference point of the first source structure and first detector structure. A second axis passes through the reference point of the second source structure and second detector structure. The first axis is parallel to the second axis, but offset to the left side of the second axis, i.e., the first and second axes are not coincident. In this eighth geometric arrangement, the first, second, and third distances are equal.

In an eleventh geometric arrangement, a first axis passes through the reference point of the first source structure and second detector structure. A second axis passes through the reference point of the second source structure and first detector structure. The first axis is parallel to the second axis, but offset to the left side of the second axis, i.e., the first and second axes are not coincident. In this ninth geometric arrangement, the second distance is less than the first distance, third distance, or both. The first distance is equal to the third distance.

In a twelfth geometric arrangement, a first axis passes through the reference point of the second source structure and first detector structure. A second axis passes through the reference point of the first source structure and second detector structure. The first axis is parallel to the second axis, but offset to the left side of the second axis, i.e., the first and second axes are not coincident. In this tenth geometric arrangement, the second distance is less than the first distance, third distance, or both. The first distance is equal to the third distance.

FIG. 26 shows a probe 2605 in a thirteenth geometric arrangement with four openings in a symmetrical source-detector arrangement. In an embodiment of a symmetrical source-detector arrangement, one side of the array (e.g., top half) is a mirror image of another side of the array (e.g., bottom half). For example, in FIG. 26 an axis 2606 running laterally through the probe and parallel to an x-axis 2625*a* divides source-detector arrangement into a top arrangement and a bottom arrangement. An axis 2607 running longitudinally through the probe, through source structures 2610*a* and 2610*b* and detector structures 2615*a* and 2615*b*, and parallel to a y-axis 2625*b* divides the first blade portion into a left-hand side and a right-hand side.

In a specific embodiment, the top arrangement and bottom arrangement are mirror images of each other. Likewise, the left-hand side and right-hand side are mirror images of each other. A first distance from source structure 2610*a* to axis 2606 is the same as a second distance from detector structure 2615*b* to axis 2606. A third distance from source structure 2610*b* is the same as a fourth distance from detector structure 2615*a* to axis 2606.

In a further embodiment, a fifth distance between a first source structure (i.e., 2610*a*) and a second source structure (i.e., 2610*b*) is different from a sixth distance between the second source structure (i.e., 2615*b*) and a first detector structure (i.e., 2615*a*). The sixth distance may be greater than the fifth distance. Furthermore, a seventh distance between a second detector structure (i.e., 2615*b*) and the first detector structure may be equal to the fifth distance.

However, many other different geometric arrangements are possible. For example, in a fourteenth geometric arrangement, the fifth, sixth, and seventh distances are equal. In a fifteenth geometric arrangement, the sixth distance is less than the fifth distance, seventh distance, or both. The fifth and seventh distances are equal. In a sixteenth geometric arrangement, the seventh distance is greater than the fifth distance, sixth distance, or both. The fifth and sixth distances are equal. In a seventeenth geometric arrangement, the fifth distance is greater than the sixth distance, seventh distance, or both. The sixth and seventh distances are equal.

FIG. 27 shows a probe 2705 in an eighteenth geometric arrangement with a slot 2710 that includes two or more source structures (e.g., 2715*a* and 2715*b*), detector structures (e.g., 2720*a* and 2720*b*), or both in a symmetrical source-detector arrangement.

In a specific implementation, the slot has the shape of an obround (i.e., a shape with two parallel sides and semicircular ends). However, the slot may be of any shape. The shape may be composed of straight line segments such as a polygon (e.g., square, rectangle, triangle, and parallelogram), composed of curved line segments (e.g., oval, ellipse, crescent, and circle), or combinations of these (e.g., semicircle and obround).

In the example shown in FIG. 27, the slot includes source structures 2715*a* and 2715*b* and detector structures 2720*a* and 2720*b*. Each source and detector structure may include an end of a fiber optic cable. For example, a first end of fiber optic cable is coupled to source structure 2715*a*. A second end of fiber optic cable is coupled to source structure 2715*b*.

A third end of fiber optic cable is coupled to detector structure 2720*a*. A fourth end of fiber optic cable is coupled to detector structure 2720*b*.

However, it should be appreciated that in various implementations, a slot may include less than four ends of fiber optic cable or more than four ends of fiber optic cable. For example, a slot may include one, two, three, four, five, six, or more than six ends of fiber optic cable. Additional fiber optic cable allows, for example, additional data points to be taken.

In implementations discussed so far in this application, each opening of the blade or probe has a single fiber associated with it. However, in further implementations of the invention, each opening of the probe may have multiple fibers—two or more—associated with it. Or, each opening of the probe may have multiple light paths or light channels associated with it.

These light paths can be used simultaneously for transmitting to tissue or receiving light from tissue. Within a single opening, there may be two source structures, two detector structures, or one source and one detector structure. And for a single probe or elevator, there may be two or more such openings with multiple light channels.

By way of example, FIG. 28 shows a probe 2805 with a single opening 2810. The single opening includes a source structure 2815 and a detector structure 2820, each of which includes an end of a single optical fiber.

A lateral axis 2825 that is parallel to an x-axis 2830*a* passes between the source structure and the detector structure. In a specific implementation, the source structure is above the lateral axis and the detector structure is below the lateral axis. In another implementation, the source structure is below the lateral axis and the detector structure is above the lateral axis.

A longitudinal axis 2835 that is parallel to a y-axis 2830*b* passes through the detector structure. A longitudinal axis 2840 that is parallel to the y-axis passes through the source structure. In an embodiment, the longitudinal axes are coincident as shown in the example in FIG. 28.

In another embodiment, the longitudinal axes are not coincident. For example, the source structure may be offset to the left-hand side or right-hand side of the detector structure. In that case, the longitudinal axes may be parallel to each other.

Although opening 2810 is shown as a circle, this opening can have any shape, including obround, oblong, oval, ellipse, square, rectangle, triangle, or other shapes as discussed elsewhere in this application.

The source and detector structures may be separated by any distance. For example, in a specific embodiment, the source and detector structures are separated by a distance of about 1.5 millimeters. In another embodiment, the source and detector structures are separated by a distance of about 5 millimeters. Thus, the separation will typically range from about 1.5 millimeters to about 5 millimeters. However, in other implementations, the separation is less than 1.5 millimeters. For example, the source and detector structures may touch each other. In other implementations, the separation is greater than 5 millimeters.

Generally, a smaller separation may result in a smaller tip which in turn results in a smaller incision. A larger separation may result in the light from the source structure penetrating deeper into the tissue before the light is received by the detector structure.

FIG. 29 shows another implementation of a probe with a single opening having multiple fibers. This implementation is similar to that described in FIG. 28, but the orientation of source and detector structures are perpendicular to the orientation in FIG. 28.

Specifically, FIG. 29 shows a probe 2905 with a single sensor opening 2910 that includes source and detector structures 2915 and 2920, respectively.

A lateral axis 2925 that is parallel to an x-axis 2930a passes through the source structure. A lateral axis 2935 that is parallel to the x-axis passes through the detector structure. In an embodiment, the lateral axes are coincident as shown in the example in FIG. 29.

In another embodiment, the lateral axes are not coincident. For example, the source structure may be offset to above or below the detector structure. In that case, the lateral axes may be parallel to each other.

A longitudinal axis 2940, that is parallel to a y-axis 2930b, passes between the source structure and the detector structure. In a specific implementation, the source and detector structures are on opposite sides of the longitudinal axis. For example, the source structure may be on the left-hand side of the longitudinal axis and the detector structure may be on the right-hand side of the longitudinal axis. In another implementation, the source structure may be on the right-hand side of the longitudinal axis and the detector structure may be on the left-hand side of the longitudinal axis.

FIG. 30 shows another implementation of a probe with a single sensor opening having multiple fibers. This implementation is similar to that described in FIG. 29, but the orientation of the fiber is at an angle compared to the orientation in FIG. 29. This angle may be any angle relative to the orientation of fibers if FIG. 29.

It should be appreciated, however, that the source and detector structures may have any arrangement. Specifically, FIG. 30 shows a probe 3005 with a single opening 3010 that includes source and detector structures 3015 and 3020, respectively. In this example, the source and detector structures are arranged at an angle relative to an x-axis 3025a and a y-axis 3025b. That is, a line 3030 passes through the source and detector structures. The line is at an angle relative to the x-axis or y-axis. The angle may be any angle including, for example, 30, 45, 60, and 90 degrees.

Figure 31:
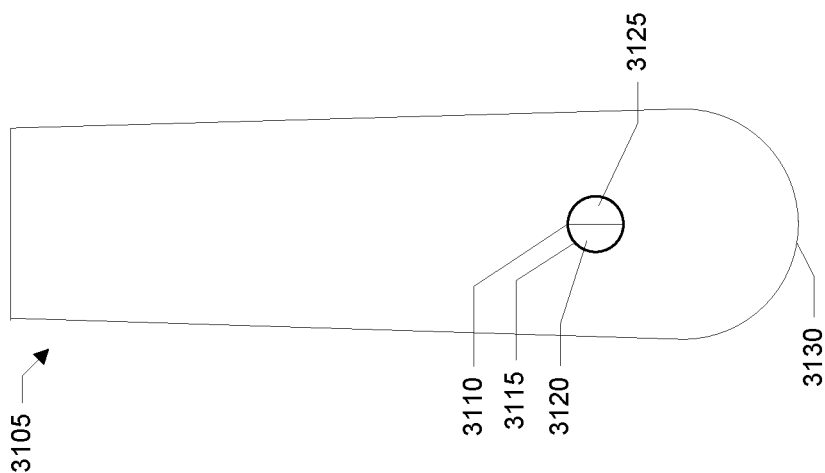
FIG. 31 shows a front view of a first blade portion with a fiber that includes multiple light channels.

FIG. 31 shows another implementation of a probe 3105 with a single sensor opening 3110 having a fiber with multiple light paths. This fiber may be referred to as a split channel fiber. There is a single circular fiber 3115 with two semicircular light channels 3120 and 3125.

In a specific implementation, light channel 3120 is a source channel and light channel 3125 is a detector channel. For example, light channel 3120 may be used to transmit light into the tissue and light channel 3125 may be used to receive light from the tissue. In another implementation, light channel 3120 is instead the detector channel and light channel 3125 is the source channel.

Although light channels 3120 and 3125 are shown as having semicircular cross sections, these light channels can have any shape. Some examples of the various shapes that they may have include polygons (e.g., square, rectangle, triangle, and parallelogram), shapes with curved line segments (e.g., oval, ellipse, and crescent), or combinations of these.

In a specific implementation as shown in FIG. 31, the light channels are symmetrical. However, in other implementations, the light channels may not be symmetrical. For example, light channel 3120 may have the shape of a square while light channel 3125 has the shape of a semicircle.

Although light channels 3120 and 3125 are shown as having the same cross-sectional areas, this is not always the case. For example, in a specific implementation, light channel 3120 may have a different cross-sectional area than light channel 3125. That is, light channel 3120 may have a greater cross-sectional area than light channel 3125 or light channel 3120 may have a smaller cross-sectional area than light channel 3125.

It should also be appreciated that a single fiber may have more light channels than the two light channels shown in FIG. 31. A single fiber may have any number of light channels.

In an embodiment, a first distance from a first light channel (e.g., 3120) to an edge 3130 of the probe is the same as a second distance from a second light channel (e.g., 3125) to the edge. However, in other embodiments, such as that shown in FIG. 32, the distances may be different.

Figure 32:
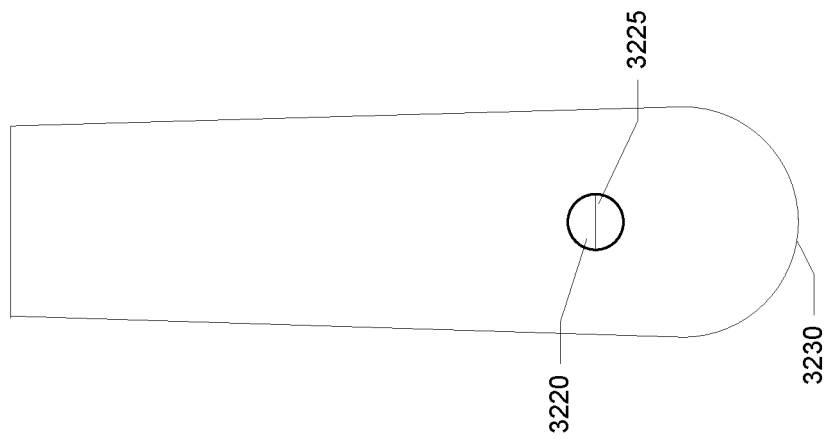
FIG. 32 shows a front view of another embodiment of a first blade portion with a fiber that includes multiple light channels.

The light channels may have any orientation. FIG. 32 shows a different orientation of the light channels where the light channels have been rotated 90 degrees from the configuration shown in FIG. 31. Any other rotation angle may be used.

In a specific embodiment, as shown in FIG. 32, a first distance from a first light channel (e.g., 3220) to an edge 3230 of the probe is different from a second distance from a second light channel (e.g., 3225) to the edge. That is, the first distance may be greater than the second distance as shown in the example of FIG. 32. In another embodiment, the first distance may be less than the second distance. In yet another embodiment, the first distance and second distance may be the same as shown in FIG. 31.

Figure 33:
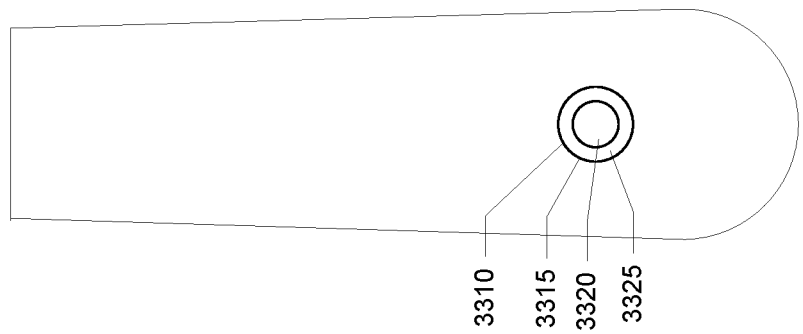
FIG. 33 shows a front view of a first blade portion with a concentric fiber that includes inner and outer light channels.

FIG. 33 shows another implementation of a probe with a single sensor opening 3310 having a fiber with multiple light channels. There is a concentric core fiber 3315 having an inner core light channel 3320, which is surrounded by an outer core light channel 3325.

In a specific implementation, the inner core light channel is a source channel and the outer core light channel is a detector channel. However, in another implementation, the inner core light channel is a detector channel and the outer core light channel is a source channel.

It should also be appreciated that the inner and outer core light channels may have any shape. Although the inner and outer core light channels are shown as circles, in various other implementations they may be shaped as polygons (e.g., square, rectangle, triangle, and parallelogram), ovals, ellipses, obrounds, or other shapes as discussed elsewhere in this application.

Furthermore, in another implementation, the inner and outer core light channels may not be concentric. For example, the inner and outer core light channels may not share the same centers.

One advantage of the single opening is that additional time and manufacturing is not expended on making multiple openings in the tip. This may result in significant cost savings which in turn may lower the overall cost of the system.

Figure 34:
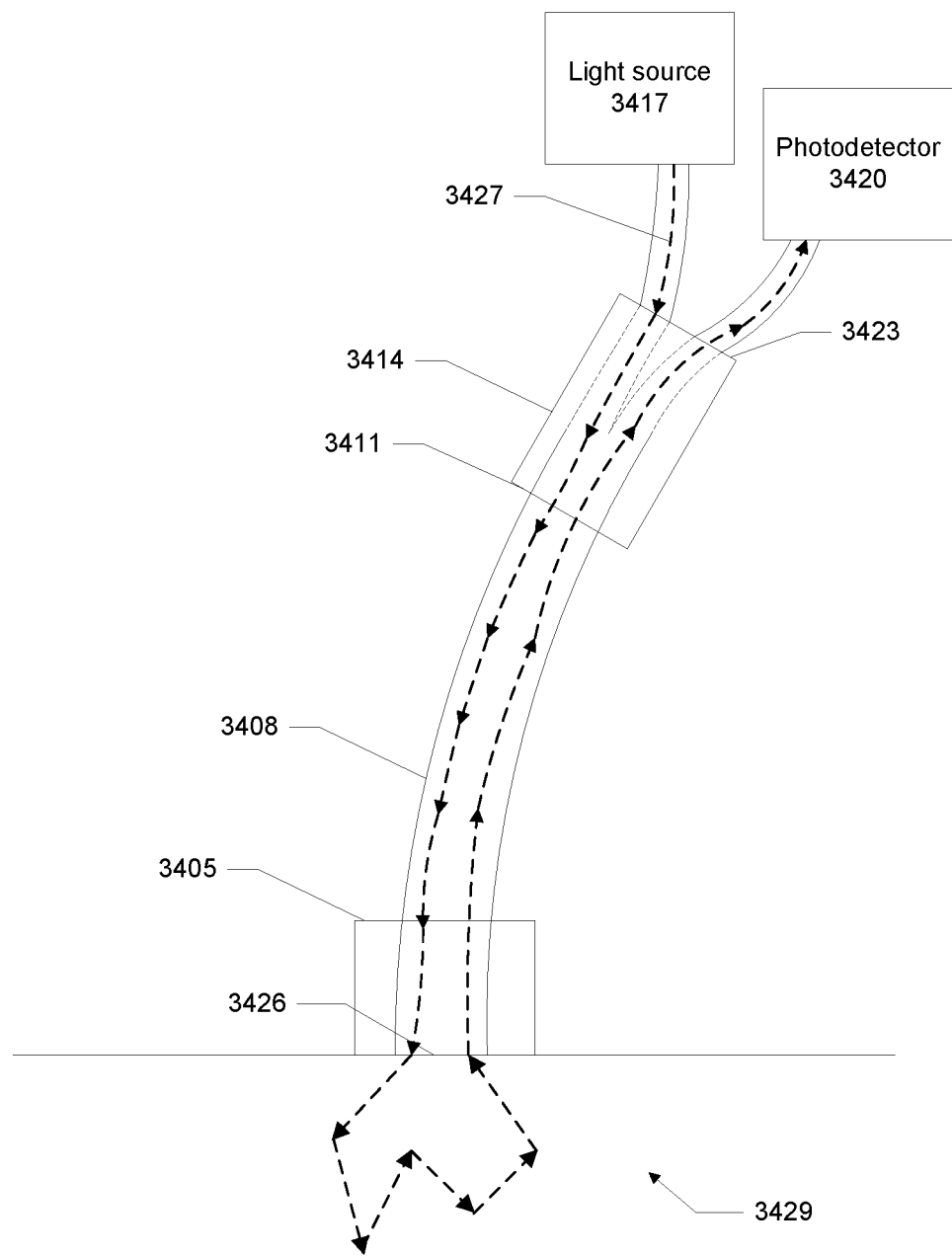
FIG. 34 shows a block diagram of an implementation of a sensor using a single optical fiber or single optical fiber bundle and a light combiner.

FIG. 34 shows a block diagram of an implementation of a sensor using a single optical fiber or single optical fiber bundle and a light combiner. A sensor head 3405 of the sensor is connected to a single fiber 3408, which is connected to a first end 3411 of a light combiner 3414. A source laser diode 3417 and photodiode detector 3420 are connected to a second end 3423 of the light combiner. The sensor head is typically attached to an opening of a probe, such as at an opening 3426 of a surgical elevator.

With this single fiber implementation, the source and detector can share one fiber. This reduces the number of optical fibers needed in implementing a sensor of the invention. Light 3427 is transmitted from light source 3417 through combiner 3414, fiber 3408, and opening 3426 to a tissue 3429 to be measured. Reflected or received light is transmitted from opening 3426, fiber 3408, and combiner 3414 to photodetector 3420. By analyzing the transmitted and received light, a determination of the oxygen saturation can be made.

In an implementation, the source laser diode is capable of outputting two or more different wavelengths of light. This permits the exposing the tissue to different wavelengths of light, such as 690 nanometers and 830 nanometers. Further in an implementation, instead of having one laser diode directly connected to the light combiner, there is another light combiner (not shown) connected in series with the light combiner. This light combiner (not shown) is, in turn, connected to two or more laser diodes, each having a different wavelength. With such a configuration, two or more wavelengths of lights from the different laser diodes can be transmitted to the sensor head through the two light combiners.

In an implementation, there may be any number of sensor openings (e.g., two, three, four, five, or more) in a probe (e.g., elevator) that are connected similarly as shown. This technique of sharing one fiber between a source and a detector reduces the number fibers and sensor openings needed. Previously, there would have been two openings, one for the source and one for the detector. For a probe with two sensor openings and two fibers connected to two light combiners according to a technique as shown in this figure, this would be equivalent to having four sensor openings—two source and two detectors—connected using the previous technique. Reducing the number of openings and fibers generally reduces the cost of the probe, which is especially desirable for making the probe disposable.

In an implementation, the light combiner is located within the monitoring console such as on a circuit board housed by the console. Locating the light combiner within the monitoring console allows, for example, the elevator to be disposed of without having to also dispose of the light combiner.

In an implementation, the light combiner is located external to the monitoring console. For example, the light combiner may be located within the handle of the elevator, along the shaft of the elevator, or within the tip of the elevator.

Further, the implementation in FIG. 34 may be used in combination with the multiple fibers or multiple light paths per single opening discussed above (i.e., see above FIGS. 28-33 and accompanying description). In particular, each light channel can be connected to a light combiner as shown as described.

The openings on the probe may have any shape. The previous implementations showed circular openings, but other shapes (e.g., square or rectangle) may be used instead.

Figure 37:
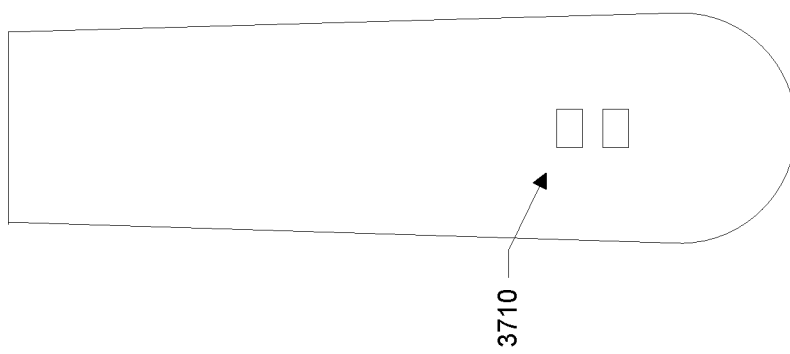
FIG. 37 shows a front view of a first blade portion with rectangular openings.
Figure 36:
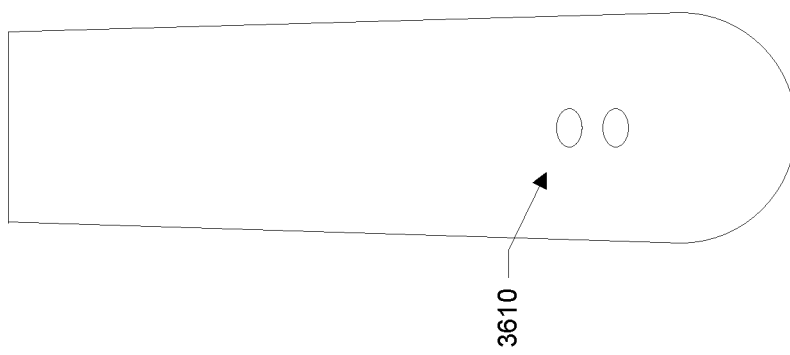
FIG. 36 shows a front view of a first blade portion with elliptical openings.
Figure 35:
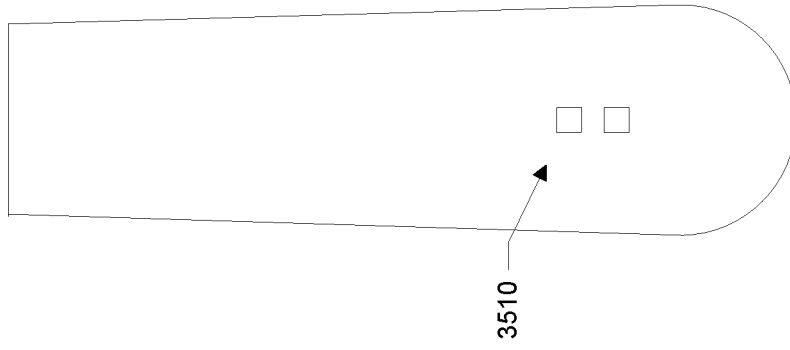
FIG. 35 shows a front view of a first blade portion with square openings.

For example, FIG. 35 shows a specific implementation of openings 3510 having square shapes. As another example, FIG. 36 shows a specific implementation of openings 3610 having elliptical shapes. In yet another example, FIG. 37 shows a specific implementation of openings 3710 having rectangular shapes. A device can have a combination of openings having different shapes (e.g., squares, ellipses, and rectangles in a single probe).

The optical fibers themselves may have the same cross-sectional shape as the openings on the probe. Or the openings themselves may have a different shape from the cross-sectional shape of the fiber. For example, a square opening can be used to hold a circular fiber. A rectangular opening can hold a circular fiber. A circular opening can hold a rectangular fiber. An oval opening can hold a square fiber. An oval opening can hold two circular fibers. An oval opening can hold a single circular fiber. As can be appreciated, many variations and combinations are possible and only a few examples are provided here.

Furthermore, in other implementations the source and detector openings may have other arrangements besides linear arrangements. For example, FIG. 38 includes source structures 3815*a* and 3815*b* and detector structures 3820*a* and 3820*b* arranged asymmetrically. The source and detector structures are arranged to form the vertices of a quadrilateral.

In an embodiment, there is a first source structure (e.g., 3815*a*), a second source structure (e.g., 3815*b*), a first detector structure (e.g., 3820*a*) including optical fiber, and a second detector structure (e.g., 3820*b*) including optical fiber. The first source structure, second source structure, first detector structure, second detector structure define vertices of a convex quadrilateral, and a first side of the quadrilateral between the first source structure and first detector structure is different in length from a second side of the quadrilateral between the second source structure and the second detector structure.

In another embodiment, there is a first source structure (e.g., 3815*a*), a second source structure (e.g., 3815*b*), a first detector structure (e.g., 3820*a*) including optical fiber, a second detector structure (e.g., 3820*b*) including optical fiber. A first distance is between the first source structure and the first detector structure, a second distance is between the first source structure and the second detector structure, a third distance is between the second source structure and the first detector structure, a fourth distance is between the second source structure and the second detector structure. The first distance is not equal to the second, third, and fourth distances, the second distance is not equal to the third and fourth distances, and the third distance is not equal to the fourth distance.

Figure 38:
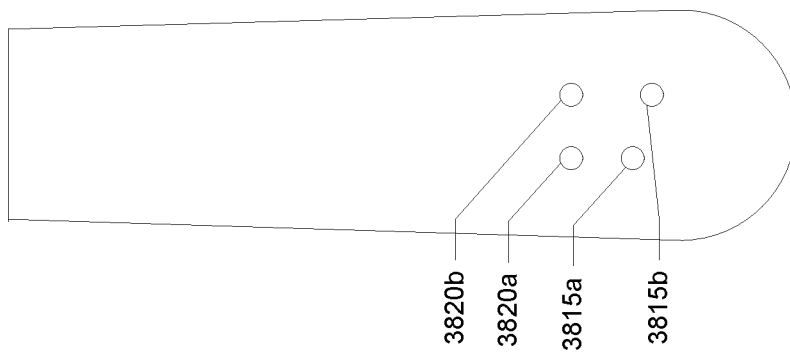
FIG. 38 shows a front view of a first blade portion with source and detector openings arranged to form the vertices of a quadrilateral.

In yet another embodiment of FIG. 38, the openings are arranged symmetrically, such as in a square, rectangle, parallelogram, or isosceles trapezoid arrangement.

The various ideas and concepts presented in this application may be combined, in any combination, with other ideas and concepts presented in this application. For example, the discussion on a single opening having multiple light channels accompanying FIGS. 28-33 is applicable to the implementation of FIG. 38. The discussion on a single optical bundle having a light combiner connected to a light source and photodetector accompanying FIG. 34 is also applicable to the implementation of FIG. 38.

Such an arrangement may be suitable where the tissue, i.e., nerve, to be measured is large enough such that the source and detector structures can be placed over the tissue. For example, such an arrangement may be used in veterinary applications where the patient may be a large animal such as a horse, cow, gorilla, tiger, lion, elephant, rhinoceros, or bull.

It should be appreciated that principles of the invention may be applied to a variety of other types of elevators that may include different angles, dimensions, contours, and so forth.

Figure 39:
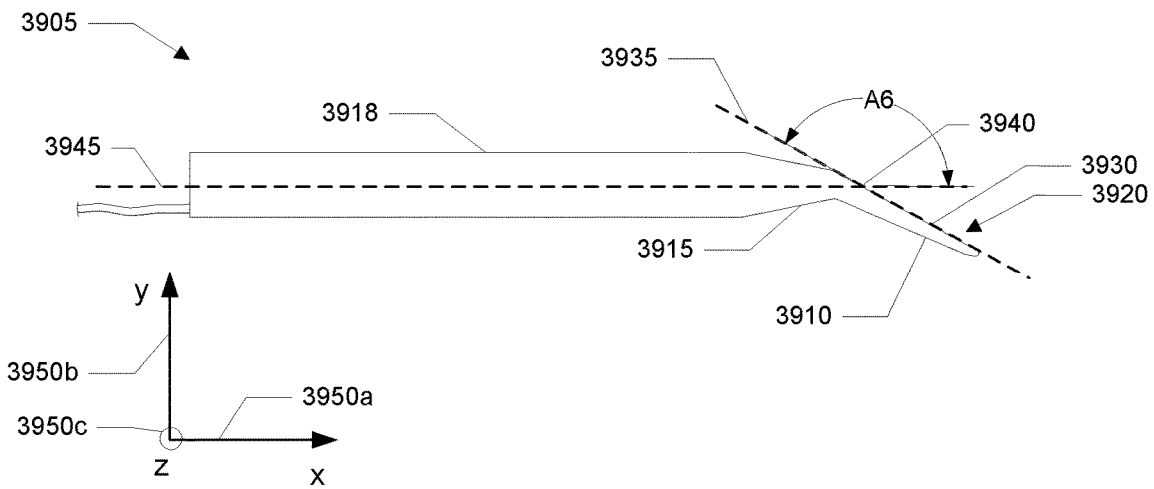
FIG. 39 shows a side view of an embodiment of an elevator with tip having a single blade.

For example, FIG. 39 shows another embodiment of a surgical elevator 3905. In this specific embodiment, the elevator includes a single blade 3910, coupled to a shaft 3915, coupled to a handle 3918. One or more openings 3920 may be included on a first surface portion 3930 of the blade.

The blade may be at an angle relative to the handle. For example, the first surface portion may lie on a plane 3935 which may be intersected at an intersection 3940 by an axis 3945 which passes longitudinally through the handle and shaft. An angle A6 is formed between plane 3935 and axis 3945.

In an embodiment, angle A6 is obtuse. In a specific embodiment, angle A6 may range from about 100 degrees to about 170 degrees. In another embodiment, angle A6 is about 120 degrees, but may range from about 105 to about 135 degrees. In a further embodiment, angle A6 may be a right angle. In yet another embodiment, angle A6 may be an acute angle.

In a specific embodiment, intersection 3940 is on the first surface portion or on the same surface as the openings. However, this is not always the case. For example, the blade may be offset along a z-axis 3950c that projects out of the page. The z-axis is relative to an x-axis 3950a and a y-axis 3050b.

Figure 40:
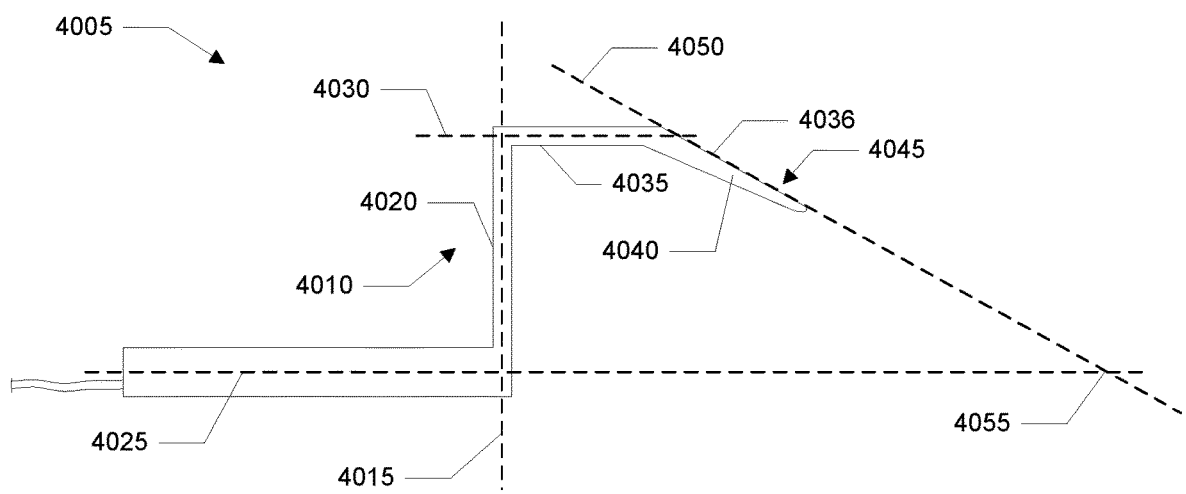
FIG. 40 shows a side view of an embodiment of an elevator with a shaft offset from the handle.

FIG. 40 shows yet another embodiment of a surgical elevator 4005 which includes a shaft 4010 that is offset from the handle. For example, an axis 4015 running through a first portion 4020 of the shaft intersects an axis 4025 running through the handle. That is, instead of the axes being coincident, the axes intersect. The axes may intersect at any angle. An axis 4030 running through a second portion 4035 of the shaft may be parallel to axis 4025 of the handle. However, in other embodiments, axis 4030 may intersect axis 4025 of the handle.

A first surface portion 4036 of a blade 4040 which may include one or more openings 4045 may lie on a plane 4050 which may be intersected at an intersection 4055 by axis 4025.

In the example shown in FIG. 40, intersection 4055 is not on the first surface portion. Instead, intersection 4055 may be located some distance away from the first surface portion.

Figure 41:
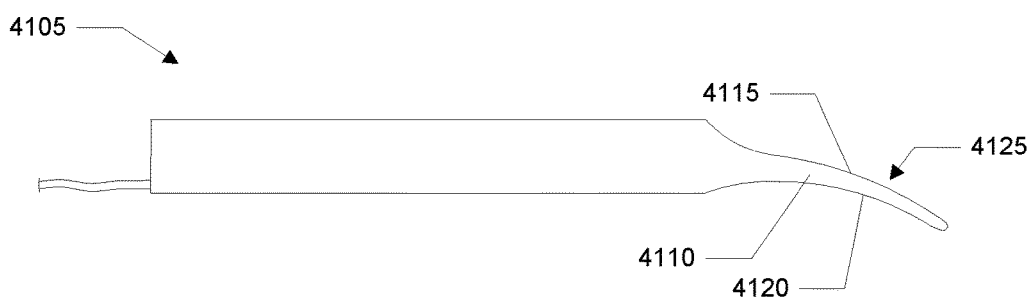
FIG. 41 shows a side view of an embodiment of an elevator with a curved tip.

FIG. 41 shows still another embodiment of a surgical elevator 4105 including a curved blade 4110. In an embodiment, the curved blade includes one or more curved surfaces that include one or more sensor openings. For example, in FIG. 41, the curved blade includes a convex surface 4115 and a concave surface 4120 that is opposite the convex surface. The convex surface may further include one or more openings 4125.

It should be appreciated that principles of the invention can be applied to a variety of different types of surgical elevators. Some examples include a Woodson elevator, Locke elevator, Carroll elevator, McKenty elevator, Sayre elevator, McGlamry elevator, Dingman Zygoma elevator, Dingman elevator, Freer elevator, Presbyterian Hospital elevator, McColloch elevator, Ballenger Septum elevator, Watson-Cheyne elevator, McDonald elevator, Pennington elevator, Howarth elevator, Cottle elevator, Kleinert-Kutz elevator, Alerdyce elevator, Ballend elevator, Penfield elevator, Sachs nerve elevator, Key elevator, Adson elevator, Joseph elevator, Williger bone elevator, Lane elevator, Crego elevator, Periosteal elevator, Hoen elevator, Sedillot elevator, Cushing elevator, Langenbeck elevator, Semb Periosteal elevator, Chandler elevator, Cobb elevator, Darrach elevator, and Wagner elevator.

Figure 42:
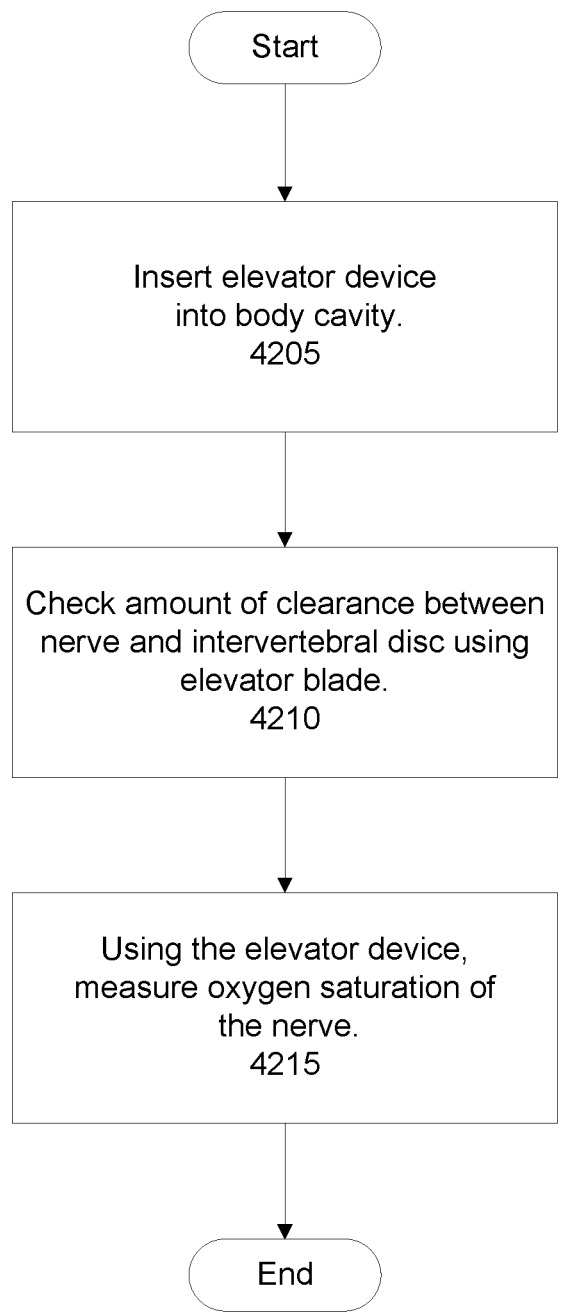
FIG. 42 shows a flow diagram representative of a user using a surgical elevator.

FIG. 42 shows a flow diagram representative of a user using an elevator. In a step 4205, the user inserts an elevator device into a body cavity. For example, the body cavity may be an incision or wound. Typically, the body cavity will be in a human, but may be in any living organism such as animals, mammals, amphibians, reptiles, horses, cows, elephants, monkeys, dogs, cats, birds, fish, and pigs.

In a step 4210, the user probes or measures the gap between the two tissues (e.g., nerve and intervertebral disc) using the tip or blade of the elevator. Typically, this is done by passing the blade across the gap and checking the amount of clearance between the nerve and intervertebral disc.

In a step 4215, the oxygen saturation of the tissue (e.g., nerve) is measured using the elevator. That is, the elevator blade may include sensor openings that face the nerve and through which light is transmitted and received. In a specific embodiment, the measurement is made using a tissue oximeter. However, the measurement may also be made using different techniques such as pulse oximetry.

Furthermore, it should also be appreciated that other types of sensors capable of oxygen sensing, including partial pressure of oxygen ($pO_2$) sensors that measure dissolved oxygen partial pressure in millimeters of mercury (mmHg) may be implemented in various embodiments of the invention. That is, the invention is not limited to a tissue oximeter as a means of oxygen sensing.

For example, a specific embodiment may include electrochemical sensors including polarographic cells, galvanic cells (i.e., ambient temperature electrochemical sensor), or both. These cells produce an electric current proportional to the number of oxygen molecules which diffuse across a membrane. A further embodiment may include a paramagnetic oxygen sensor including static paramagnetic cells, dynamic paramagnetic cells, or both. A further embodiment may include zirconium oxide cells and the use of luminescence polarization.

Figure 43:
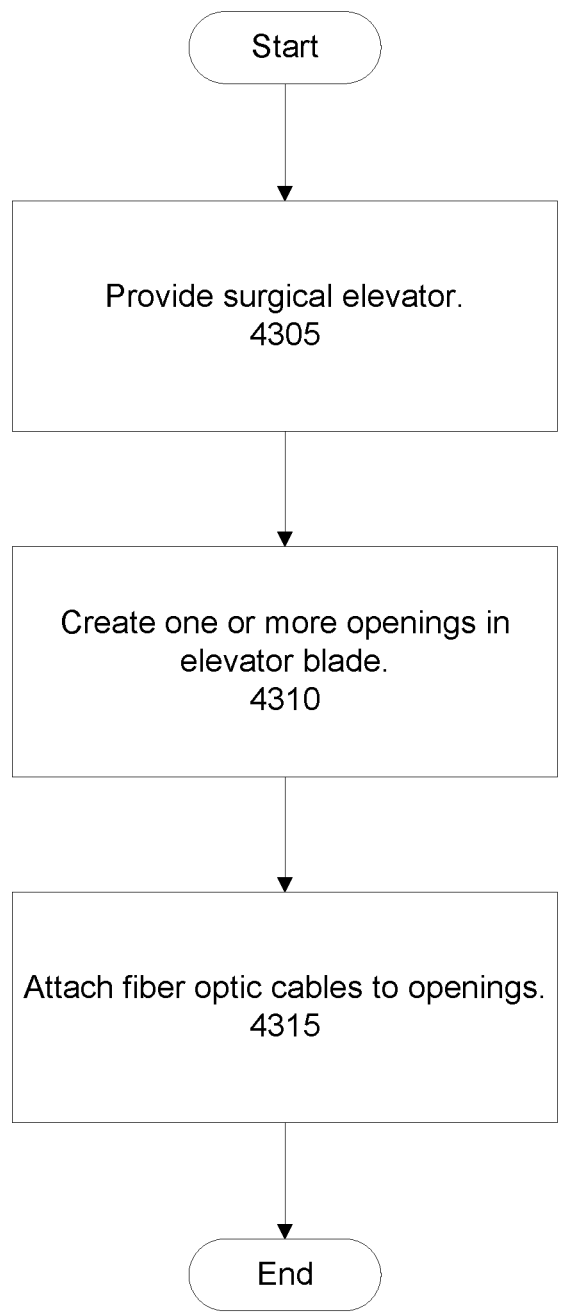
FIG. 43 shows a flow diagram representative of making a surgical elevator.

FIG. 43 shows a flow diagram representative of the steps to create a surgical elevator. In a step 4305 a surgical elevator is provided. In a specific embodiment, the elevator includes a blade with a tapered thickness, such as a Woodson elevator. However, in other embodiments, other types of elevators may be used such as those discussed above (e.g., Locke elevator, Carroll elevator, McKenty elevator, Sayre elevator, and so forth). In yet another embodiment, the elevator includes a blade with a constant thickness.

In a step 4310, one or more openings are created. For example, a first opening may be created in a first position and a second opening may be created in a second position. In a specific embodiment, such as an embodiment in which the blade has a tapered thickness, the length of the second opening may be different from the length of the first opening. That is, the length of the first opening may be greater than the length of the second opening. In another embodiment, the length of the first opening may be less than the length of the second opening.

In a specific embodiment, such as an embodiment in which the blade has a constant thickness, the length of the first and second openings may be the same.

The one or more openings may be created by drilling, punching, stamping, milling, casting, or the like.

In a step 4315, cables such as optical fiber cables are attached to the one or more openings. The cables may be secured to the openings using, for example, an adhesive (e.g., epoxy). The adhesive may be applied such that the adhesive covers an entire side of the blade. In a specific embodiment, the adhesive may be sculpted (e.g., tapered). In one embodiment, the sculpting may be performed before the adhesive has cured. In another embodiment, the sculpting may be performed after the adhesive has cured.

As discussed above, it should also be appreciated that principles of the invention may also be applied to endoscopes. Endoscopes are typically used to observe portions various body cavities, such as the interior surfaces of an organ during an endoscopy. In a specific embodiment, an endoscope includes a sensor unit (e.g., source fiber and detector fiber) mounted to the endoscope. The sensor unit may be mounted to the tip of the endoscope. The combination allows both observation of the tissue and an oxygen measurement of the tissue.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
providing a metal blade having a tapered thickness;
creating a first opening through the blade at a first position;
creating a second opening though the blade at a second position, wherein the second opening has a length different from the first opening;
attaching a first optical fiber to the blade at the first opening;
attaching a second optical fiber to the blade at the second opening; and
covering the first and second optical fibers with an adhesive material.

2. The method of claim 1 wherein the blade comprises a first portion and a second portion, the first portion being angled with respect to the second portion, and the first and second openings are in the first portion.

3. The method of claim 1 wherein the blade is coupled to an elongated handle and the first and second optical fibers are run along the elongated handle.

4. The method of claim 1 wherein the adhesive material covers an entirety of one side of the metal blade.

5. The method of claim 1 wherein the adhesive material comprises an epoxy.

6. A method of operating a device comprising a blade comprising
a first side and a second side, wherein a first opening passes from the first side to the second side of the blade,
a second opening passes from the first side to the second side of the blade, and a first length of the first opening is less than a second length of the second opening,
a first optical fiber coupled to the first opening, and
a second optical fiber coupled to the second opening, the method comprising:
emitting a first radiation emission through the first optical fiber to the first opening;
receiving a second radiation emission at the second opening and transmitting the second radiation emission through the second optical fiber; and
calculating a value based on quantities for the first radiation emission and second radiation emission and a distance between the first and second openings.

7. The method of claim 6 wherein the second radiation emission is an attenuated reflection of the first radiation emission.

8. A method comprising:
providing a handle, wherein the handle comprises an axis;
coupling a blade to the handle, wherein the blade comprises a first blade portion and a second blade portion, the blade is metal, the first blade portion comprises a first side and a second side, and the second blade portion is between the first blade portion and the handle;
positioning the first blade portion at a first angle in a first rotation direction relative to the handle's axis;
positioning the second blade portion at a second angle in a second rotation direction relative to the first blade portion, where the second rotation direction is opposite of the first rotation direction;
forming a first opening that passes from the first side to the second side of the blade;
forming a second opening that passes from the first side to the second side of the first blade portion;
coupling a first optical fiber to the first opening;
coupling a second optical fiber to the second opening; and
covering the first and second optical fibers and the first and second openings on the first side with an epoxy,
wherein the first and second openings are unconcealed on the second side and a distal end of the blade is rounded and the epoxy covers at least a portion of the first side without covering the second side.

9. The method of claim 8 wherein the distal end has a thickness of about 2 millimeters or less.

10. The method of claim 8 wherein a thickness between the first side and second side of the blade is tapered, decreasing in thickness from a proximal end of the blade to the distal end of the blade.

11. The method of claim 10 wherein the first blade portion comprises a flat section and the second blade portion comprises a flat section.

12. The method of claim 8 wherein a surface of the epoxy is rounded from a first side edge to a second side edge of the blade.

13. The method of claim 12 wherein a thickness of the epoxy is greater over the first and second openings than at the first and second side edges.

14. The method of claim 13 wherein the first blade portion comprises a flat section and the second blade portion comprises a flat section.

15. The method of claim 8 wherein a line passing through the first and second openings on the second side is parallel with a first side edge along the second side of the blade.

16. The method of claim 15 wherein a first distance from the first opening to the first side edge is the same as a second distance from the first opening to a second side edge, opposite of the first side edge.

17. The method of claim 16 wherein the first side edge is parallel to the second side edge.

18. The method of claim 8 wherein a first distance from the first opening to the distal end is shorter than a second distance from the first opening to a proximal end.

19. The method of claim 18 wherein a third distance from the second opening to the distal end is longer than the first distance.

20. The method of claim 8 wherein the first side of the first blade portion faces toward the handle and the second side of the first blade portion faces away from the handle.

21. The method of claim 8 wherein the second angle between the first and second blade portions is in a range between about 90 degrees and 170 degrees.

22. The method of claim 8 wherein the blade comprises at most two openings.

23. The method of claim 8 wherein the first optical fiber is a split optical fiber capable of carrying at least two optical channels.

24. The method of claim 8 wherein the first optical fiber is a concentric optical fiber capable of carrying at least two optical channels.

25. The method of claim 8 wherein the first blade portion comprises a flat section and the second blade portion comprises a flat section.

26. The method of claim 8 wherein the first and second optical fibers run through the epoxy and exit the epoxy covering the first and second openings.

27. The method of claim 8 wherein a thickness of at least the first blade portion or the epoxy corresponds to a desired separation gap between a patient's tissue, nerve, or bone.

28. The method of claim 8 comprising:
providing an alert indicator, wherein the alert indicator generates an alert when an oxygen saturation level for a patient determined using the first and second optical fibers falls below a threshold value.

29. The method of claim 8 comprising:
providing an alert indicator, wherein the alert indicator generates an alert when at least one of the first or second optical fibers receives light reflected from a patient's tissue indicating that the first blade portion is positioned at a suitable location.

30. The method of claim 8 comprising:
mounting an electronic component on the second side of the blade.

31. The method of claim 30 wherein the electronic component is at least one of a printed circuit board comprising power and ground wires, a thin-film circuit board, a photodetector, a light emitting diode, or a laser diode.

32. The method of claim 30 wherein the electronic component mounted on the second side of the blade is a first electronic component, and the method comprises
mounting a second electronic component on the first side of the blade.

33. The method of claim 30 wherein the electronic component mounted on the second side of the blade is a first electronic component, and the blade comprises a cavity within which the first electronic component is mounted.

34. The method of claim 30 wherein the first blade portion comprises a flat section and the second blade portion comprises a flat section.

35. The method of claim 8 comprising:
mounting an electronic component on the first side of the blade.

36. The method of claim 35 wherein the electronic component is at least one of a printed circuit board comprising power and ground wires, a thin-film circuit board, a photodetector, a light emitting diode, or a laser diode.

37. The method of claim 35 wherein the second opening is below the electronic component.

* * * * *